US012079960B2

(12) United States Patent
Clark et al.

(10) Patent No.: US 12,079,960 B2
(45) Date of Patent: Sep. 3, 2024

(54) SYSTEMS, DEVICES, AND METHODS FOR HARMONIZATION OF IMAGING DATASETS INCLUDING BIOMARKERS

(71) Applicants: TERRAN BIOSCIENCES INC., New York, NY (US); THE TRUSTEES OF COLUMBIA UNIVERSITY IN THE CITY OF NEW YORK, New York, NY (US); THE RESEARCH FOUNDATION FOR MENTAL HYGIENE, INC., Menands, NY (US)

(72) Inventors: Samuel Clark, New York, NY (US); Kenneth Wengler, New York, NY (US); Guillermo Horga Hernandez, New York, NY (US)

(73) Assignees: Terran Biosciences Inc., Miami Beach, FL (US); The Trustees of Columbia University in the City of New York, New York, NY (US); The Research Foundation for Mental Hygiene, Inc., Menands, NY (US)

( * ) Notice: Subject to any disclaimer, the term of this patent is extended or adjusted under 35 U.S.C. 154(b) by 283 days.

(21) Appl. No.: 17/693,166

(22) Filed: Mar. 11, 2022

(65) Prior Publication Data

US 2022/0292657 A1 Sep. 15, 2022

Related U.S. Application Data

(60) Provisional application No. 63/159,915, filed on Mar. 11, 2021.

(51) Int. Cl.
*G06T 5/50* (2006.01)
*A61B 5/055* (2006.01)
(Continued)

(52) U.S. Cl.
CPC .............. *G06T 5/50* (2013.01); *A61B 5/055* (2013.01); *G06T 5/90* (2024.01); *G06T 7/0014* (2013.01);
(Continued)

(58) Field of Classification Search
CPC .......... G06T 5/50; G06T 5/90; G06T 7/0014; G06T 2207/10088; G06T 2207/20081;
(Continued)

(56) References Cited

U.S. PATENT DOCUMENTS 6,321,105 B1 11/2001 Jenkins et al.
11,810,334 B2 * 11/2023 Kamali-Zare ........ A61B 5/4094
(Continued)

FOREIGN PATENT DOCUMENTS

| CN | 116528747 | * | 8/2021 | ............. A61B 5/055 |
| JP | 6746160 | * | 8/2020 | ............. G26H 50/20 |

(Continued)

OTHER PUBLICATIONS

Abi-Dargham et al. "The search for imaging biomarkers in psychiatric disorders", Nature Medicine, (Nov. 2016); 22(11):1248-1255.
(Continued)

*Primary Examiner* — Jerome Grant, II
(74) *Attorney, Agent, or Firm* — COOLEY LLP; Heidi A. Erlacher; Eric A. Owens

(57) ABSTRACT

An exemplary system, method and computer-accessible medium for harmonizing neuromelanin (NM) data using combat directly on a NM database or using combat generated coefficients to harmonize future data can include, for example, receiving imaging information of a brain of the patient(s), from one MRI scanner, receiving imaging information of a brain of the patient(s), from a second MRI scanner and using combat to harmonize the data between scanners against a reference dataset. The Neuromelanin
(Continued)

(NM) concentration of the patient(s) can then be determined based on the harmonized data. The NM concentration can be determined using a voxel-wise analysis procedure. The voxel-wise analysis procedure can be used to determine a topographical pattern(s) within a substantia nigra (SN) of the brain of the patient(s).

**18 Claims, 18 Drawing Sheets
(2 of 18 Drawing Sheet(s) Filed in Color)**

(51) Int. Cl.
G06T 5/90 (2024.01)
G06T 7/00 (2017.01)
G16H 50/20 (2018.01)

(52) U.S. Cl.
CPC ... *G16H 50/20* (2018.01); *G06T 2207/10088* (2013.01); *G06T 2207/20081* (2013.01); *G06T 2207/30016* (2013.01)

(58) Field of Classification Search
CPC .......... G06T 2207/30016; A61B 5/055; G16H 50/20; G16H 15/00; G16H 20/70; G16H 50/70; G16H 70/20; G16H 30/40; G01R 33/5608
USPC ....................................................... 382/131
See application file for complete search history.

(56) References Cited

U.S. PATENT DOCUMENTS

| | | | |
|---|---|---|---|
| 2002/0115930 A1 | 8/2002 | Hutchinson | |
| 2005/0260577 A1 | 11/2005 | Double et al. | |
| 2007/0275944 A1 | 11/2007 | Sharpe | |
| 2009/0041800 A1 | 2/2009 | Woiwode et al. | |
| 2012/0209110 A1 | 8/2012 | Bankiewicz et al. | |
| 2015/0010223 A1 | 1/2015 | Sapiro et al. | |
| 2015/0023877 A1 | 1/2015 | Bu et al. | |
| 2019/0049466 A1 | 2/2019 | Bolotina | |
| 2021/0123999 A1* | 4/2021 | An ........................ G01R 33/567 |
| 2021/0228144 A1 | 7/2021 | Hernandez et al. | |
| 2022/0273184 A1 | 9/2022 | Clark et al. | |
| 2023/0200716 A1 | 6/2023 | Hernandez et al. | |

FOREIGN PATENT DOCUMENTS

| | | | | |
|---|---|---|---|---|
| JP | 6942278 | * | 9/2022 | ........... G06T 7/0012 |
| KR | 102245189 B1 | | 4/2021 | |
| KR | 102256345 | * | 5/2021 | ........... A61B 5/7264 |
| WO | WO-0231499 A1 | | 4/2002 | |
| WO | WO-2014071359 A1 | | 5/2014 | |
| WO | WO-2017007696 A1 | | 1/2017 | |
| WO | WO-2017192952 A1 | | 11/2017 | |
| WO | WO-2019178336 A1 | | 9/2019 | |
| WO | WO-2020077098 A1 | | 4/2020 | |
| WO | WO-2021034770 A1 | | 2/2021 | |
| WO | WO-2022040137 A1 | | 2/2022 | |
| WO | 2022104288 | * | 5/2022 | ........... A61B 5/4088 |
| WO | WO-2022104288 A1 | | 5/2022 | |
| WO | WO-2022192728 A2 | | 9/2022 | |

OTHER PUBLICATIONS

Aiba et al. "Neuromelanin-sensitive MRI in the differential diagnosis of elderly white matter lesion from Parkinson's disease", Neurology and Clinical Neuroscience, (Nov. 2019); 7(6):322-325.
Andersson et al. "Non-linear registration, aka Spatial normalisation FMRIB technical report TR07JA2", FMRIB Analysis Group of the University of Oxford, (Jun. 28, 2007); 2(1):e21, 22 pages.
Ashburner et al. "Unified segmentation", Neuroimage, (Feb. 2005); 26(3):839-851.
Ashburner J. "A fast diffeomorphic image registration algorithm", Neuroimage, (Jul. 2007); 38(1):95-113.
Avants et al. "Advanced normalization tools (ANTS)", Insight J, (Jun. 4, 2009); 2(365):1-35.
Avants et al. "Symmetric diffeomorphic image registration with cross-correlation: evaluating automated labeling of elderly and neurodegenerative brain", Medical Image Analysis, (Jun. 2007); 12(1):26-41.
Bae et al. "Loss of nigral hyperintensity on 3 Tesla MRI of parkinsonism: comparison with 123I-FP-CIT SPECT", Movement Disorders, (Dec. 2016); 31(5):684-692.
Betts et al. "In vivo MRI assessment of the human locus coeruleus along its rostrocaudal extent in young and older adults", Neuroimage, (Oct. 2016); 163:150-159.
Betts et al. "Locus coeruleus imaging as a biomarker for noradrenergic dysfunction in neurodegenerative diseases", Brain, (May 2019); 142(9):2558-2571.
Blazejewska et al. "Visualization of nigrosome 1 and its loss in PD: pathoanatomical correlation and in vivo 7 T MRI", Neurology, (Jul. 2013); 81(6):534-540.
Braak et al. "Frequency of stages of Alzheimer-related lesions in different age categories", Neurobiology of Aging, (Jan. 1997); 18(4):351-357.
Braak et al. "Stages of the pathologic process in Alzheimer disease: age categories from 1 to 100 years", Journal of Neuropathology & Experimental Neurology, (Nov. 2011); 70(11):960-969.
Braak et al. "Staging of Alzheimer disease-associated neurofibrillary pathology using paraffin sections and immunocytochemistry", Acta Neuropathologica, (Aug. 2006); 112(4):389-404.
Brett et al. "Using the Talairach atlas with the MNI template", Neuroimage, (2001); 13(6):S85, 1 page, Dec. 2001.
Cassidy et al. "194. Neuromelanin-Sensitive MRI as an Early Indicator of Dopamine Dysfunction in Individuals at Risk for Psychosis", Schizophrenia Bulletin, (2017); 43(Suppl 1):S101, 1 page.
Cassidy et al. "S236. Neuromelanin-Sensitive MRI: A Novel, Non-Invasive Proxy Measure of Dopamine Function in Neuropsychiatric Illness", Biological Psychiatry, (2018); 83(9):S440, 4 pages, Feb. 2018.
Cassidy et al. "A perceptual inference mechanism for hallucinations linked to striatal dopamine", Current Biology, (2018); 28(4):503-514, Dec. 2017.
Cassidy et al. "Evidence for dopamine abnormalities in the substantia nigra in cocaine addiction revealed by neuromelanin-sensitive MRI", American Journal of Psychiatry, (2020); 177(11):1038-1047, Jun. 2020.
Cassidy et al. "Neuromelanin-sensitive MRI as a noninvasive proxy measure of dopamine function in the human brain", Proceedings of the National Academy of Sciences, (2019); 116(11):5108-5117, Jan. 2019.
Cassidy et al. "Neuromelanin-sensitive MRI as a proxy measure of dopamine function in neuropsychiatric illness", Dopamine Conference, (Aug. 2016), 2 pages.
Castellanos et al. "Automated Neuromelanin Imaging as a Diagnostic Biomarker for Parkinson's Disease", Movement Disorders, (Jun. 2015); 30(7):945-952.
Chen X., et al., Detecting Alterations in Caudal Portion of Substantia Nigra in Parkinson's Disease, Proc. Intl. Soc. Mag. Reson. Med., Jun. 2015, p. 4286.
Chen X. et al. "Simultaneous imaging of locus coeruleus and substantia nigra with a quantitative neuromelanin MRI approach", Magnetic Resonance Imaging, (2014); 32(10):1301-1306, Jul. 2014.
Chen Y, et al. "Voxel-level comparison of arterial spin-labeled perfusion MRI and FDG-PET in Alzheimer disease", Neurology, (Dec. 2011); 77(22):1977-1985.
Clewett et al. "Neuromelanin marks the spot: identifying a locus coeruleus biomarker of cognitive reserve in healthy aging", Neurobiology of Aging, (2016); 37:117-126, Sep. 2015.
Cselenyi et al. "Clinical validation of 18F-AZD4694, an amyloid-β-specific PET radioligand", Journal of Nuclear Medicine, (2012); 53(3):415-424, Mar. 2012.

(56) References Cited

OTHER PUBLICATIONS

Dordevic et al. "Optimal cut-off value for locus coeruleus-to-pons intensity ratio as clinical biomarker for Alzheimer's disease: a pilot study", Journal of Alzheimer's Disease Reports, (2017); 1(1):159-167, Oct. 2017.

Dubois et al. "Characterization of age/sex and the regional distribution of mglur5 availability in the healthy human brain measured by high-resolution [11 c] abp688 pet", European Journal of Nuclear Medicine and Molecular Imaging, (Aug. 2015); 43:152-162.

Eapen et al. "Using high-resolution MR imaging at 7T to evaluate the anatomy of the midbrain dopaminergic system", American Journal of Neuroradiology, (Apr. 2011), 32(4):688-694.

Enochs et al. "Paramagnetic metal scavenging by melanin: MR imaging", Radiology, (1997); 204(2):417-423, Apr. 1997.

Fabbri et al. "Substantia nigra neuromelanin as an imaging biomarker of disease progression in Parkinson's disease", Journal of Parkinson's Disease, (2017); 7(3):491-501, Jun. 2017.

Griswold et al. "Generalized autocalibrating partially parallel acquisitions (GRAPPA)", Magnetic Resonance in Medicine: An Official Journal of the International Society for Magnetic Resonance in Medicine, (2002); 47(6):1202-1210, Jan. 2002.

Grothe et al. "Alzheimer's Disease Neuroimaging Initiative. In vivo staging of regional amyloid deposition", Neurology, (2017); 89(20):2031-2038, Nov. 2017.

Groveman et al. "Rapid and ultra-sensitive quantitation of disease-associated α-synuclein seeds in brain and cerebrospinal fluid by αSyn RT-QuIC", Acta Neuropathologica Communications, (Feb. 2018); 6(1):1-10.

Guo et al. "Dopamine depletion and in vivo binding of PET D1 receptor radioligands: implications for imaging studies in schizophrenia", Neuropsychopharmacology, (2003); 28(9):1703-1711.

Guo et al. "Impact of D2 receptor internalization on binding affinity of neuroimaging radiotracers", Neuropsychopharmacology, (Oct. 2009); 35(3):806-817.

Hatano et al "Neuromelanin MRI is useful for monitoring motor complications in Parkinson's and PARK2 disease", Journal of Neural Transmission, (2017); 124(4):407-415, Jan. 2017.

Hirsch et al. "Melanized dopaminergic neurons are differentially susceptible to degeneration in Parkinson's disease", Nature, (1988); 334(6180):345-348, Jul. 1998.

Huddleston et al. "In vivo detection of lateral-ventral tier nigral degeneration in Parkinson's disease", Human Brain Mapping, (Feb. 2017); 38(5):2627-2634.

Isaias et al. "Neuromelanin imaging and dopaminergic loss in Parkinson's disease", Frontiers in Aging Neuroscience, (2016); 8(196):1-12, Aug. 2016.

Ito H. et al. "Normative data of dopaminergic neurotransmission functions in substantia nigra measured with MRI and PET: Neuromelanin, dopamine synthesis, dopamine transporters, and dopamine D2 receptors", Neuroimage, (2017); 158:12-17, Jun. 2017.

Jacobs et al. "Dynamic behavior of the locus coeruleus during arousal-related memory processing in a multi-modal 7T fMRI paradigm", Elife, (2020); 9:e52059, 30 pages, 6+–.

Kashihara et al. "Neuromelanin magnetic resonance imaging of nigral volume loss in patients with Parkinson's disease", Journal of Clinical Neuroscience, (2011); 18(8):1093-1096, Dec. 2011.

Kashihara et al. "Reduction of neuromelanin-positive nigral volume in patients with MSA, PSP and CBD", Internal Medicine, (2011); 50(16):1683-1687, Apr. 2011.

Keren et al. "In vivo mapping of the human locus coeruleus", Neuroimage, (2009); 47(4):1261-1267.

Kitao et al. "Correlation between pathology and neuromelanin MR imaging in Parkinson's disease and dementia with Lewy bodies", Neuroradiology, (2013); 55:947-953, Apr. 2013.

Klein et al. "Evaluation of 14 nonlinear deformation algorithms applied to human brain MRI registration", Neuroimage, (2009); 46(3):786-802, Jan. 2009.

Kuya et al. "Correlation between neuromelanin-sensitive MR imaging and 123 I-FP-CIT SPECT in patients with parkinsonism", Neuroradiology, (2016); 58:351-356, Jan. 2016.

Langley et al. "A multicontrast approach for comprehensive imaging of substantia nigra", Neuroimage, (2015); 112:7-13, Feb. 2015.

Langley et al. "Reproducibility of locus coeruleus and substantia nigra imaging with neuromelanin sensitive MRI", Magnetic Resonance Materials in Physics, Biology and Medicine, (Apr. 2016); 30:121-125.

Lee et al. "Specific visualization of neuromelanin-iron complex and ferric iron in the human post-mortem substantia nigra using MR relaxometry at 7T", Neuroimage, (Nov. 2017); 172:874-885.

Li et al. "Structural and cognitive deficits in remitting and non-remitting recurrent depression: a voxel-based morphometric study", Neuroimage, (Nov. 2009); 50(1):347-356.

Liang et al. "Inverse relationship between the contents of neuromelanin pigment and the vesicular monoamine transporter-2: human midbrain dopamine neurons", Journal of Comparative Neurology, (2004); 473(1):97-106.

Liebe et al. "In vivo anatomical mapping of human locus coeruleus functional connectivity at 3 T MRI", Human Brain Mapping, (2020); 41(8):2136-2151, Jan. 2020.

Liu et al. "In vivo visualization of age-related differences in the locus coeruleus", Neurobiology of Aging, (2019); 74:101-111, Nov. 2018.

Mahlknecht et al. "Meta-analysis of dorsolateral nigral hyperintensity on magnetic resonance imaging as a marker for Parkinson's disease", Movement Disorders, (Dec. 2016); 32(4):619-623.

Martin-Bastida et al. "Relationship between neuromelanin and dopamine terminals within the Parkinson's nigrostriatal system", Brain, (2019); 142(7):2023-2036, Mar. 2019.

Mather et al. "Higher locus coeruleus MRI contrast is associated with lower parasympathetic influence over heart rate variability", Neuroimage, (2017); 150:329-335, Oct. 2017.

Mathotaarachchi et al. "Identifying incipient dementia individuals using machine learning and amyloid imaging", Neurobiology of Aging, (2017); 59:80-90, Nov. 2017.

Mathotaarachchi et al. "VoxelStats: a MATLAB package for multi-modal voxel-wise brain image analysis", Frontiers in Neuroinformatics, (2016); 10(20):1-12, Jun. 2016.

Matsuura et al. "A longitudinal study of neuromelanin-sensitive magnetic resonance imaging in Parkinson's disease", Neuroscience Letters, (2016); 633:112-117, Sep. 2016.

Matsuura et al. "Neuromelanin magnetic resonance imaging in Parkinson's disease and multiple system atrophy", European Neurology, (2013); 70(1-2):70-77, Jun. 2013.

Mazziotta et al. "A probabilistic atlas of the human brain: theory and rationale for its development", Neuroimage, (1995); 2(2):89-101, Apr. 1995.

Menke et al. "MRI characteristics of the substantia nigra in Parkinson's disease: a combined quantitative T1 and DTI study", Neuroimage, (2009); 47(2):435-441, May 2009.

Miyoshi et al. "Evaluation of Parkinson disease and Alzheimer disease with the use of neuromelanin MR imaging and 123I-metaiodobenzylguanidine scintigraphy", American Journal of Neuroradiology, (2013); 34(11):2113-2118, Jan. 2013.

Morris et al. Sub-millimeter variation in human locus coeruleus is associated with dimensional measures of psychopathology: An in vivo ultra-high field 7-Tesla MRI study, NeuroImage: Clinical, (2020); 25(102148): 1-8, Jan. 2020.

Nakamura et al. "Neuromelanin-sensitive magnetic resonance imaging: a promising technique for depicting tissue characteristics containing neuromelanin", Neural Regeneration Research, (2014); 9(7):759-760, Apr. 2014.

Ogisu et al. "3D neuromelanin-sensitive magnetic resonance imaging with semi-automated volume measurement of the substantia nigra pars compacta for diagnosis of Parkinson's disease", Neuroradiology, (2013); 55:719-724, Mar. 2013.

Ohtsuka et al. "Changes in substantia nigra and locus coeruleus in patients with early-stage Parkinson's disease using neuromelanin-sensitive MR imaging", Neuroscience Letters, (2013); 541:93-98, Feb. 2013.

(56) References Cited

OTHER PUBLICATIONS

Ohtsuka et al. "Differentiation of early-stage parkinsonisms using neuromelanin-sensitive magnetic resonance imaging", Parkinsonism & Related Disorders, (2014); 20(7):755-760, Apr. 2014.
Pascoal et al. "In vivo quantification of neurofibrillary tangles with [18F] MK-6240", Alzheimer's Research & Therapy, (2018); 10(1):1-4, Jul. 2018.
Priovoulos et al. "High-resolution in vivo imaging of human locus coeruleus by magnetization transfer MRI at 3T and 7T", Neuroimage, (2018); 168:427-436, Jul. 2017.
Rajtmajer et al. "A voxelwise approach to determine consensus regions-of-interest for the study of brain network plasticity", Frontiers in Neuroanatomy, (2015); 9(97):1-13, Jul. 2015.
Rice et al. "Mapping dopaminergic deficiencies in the substantia nigra/ventral tegmental area in schizophrenia", Brain Structure and Function, (2016); 221:185-201, Sep. 2014.
Robson et al. "Comprehensive quantification of signal-to-noise ratio and g-factor for image-based and k-space-based parallel imaging reconstructions", Magnetic Resonance in Medicine: An Official Journal of the International Society for Magnetic Resonance in Medicine, (2008); 60(4):895-907, Oct. 2008.
Rowley et al. "White matter abnormalities and structural hippocampal disconnections in amnestic mild cognitive impairment and Alzheimer's disease", PloS One, (2013); 8(9):e74776, 13 pages, Sep. 2013.
Sasaki et al. "Neuromelanin magnetic resonance imaging of locus ceruleus and substantia nigra in Parkinson's disease", Neuroreport, (2006); 17(11):1215-1218, May 2006.
Sasaki et al. "Neuromelaninsensitive MRT. Grundlagen, Technik und klinische Einsatzmöglichkeiten: Basics, Technique, and Clinical Applications", Clinical Neuroradiology, (2008); 18:147-153, Jul. 2008.
Sasaki et al. "Visual discrimination among patients with depression and schizophrenia and healthy individuals using semiquantitative color-coded fast spin-echo T1-weighted magnetic resonance imaging", Neuroradiology, (2010); 52:83-89, Aug. 2009.
Schwarz et al. "Magnetisation transfer contrast to enhance detection of neuromelanin loss at 3T in Parkinson's disease", InProc. Int. Soc. Mag. Reson. Med., (2013); 21(2848): 1 page, Dec. 2013.
Schwarz et al. "T1-weighted MRI shows stage-dependent substantia nigra signal loss in Parkinson's disease", Movement Disorders, (Jan. 2010); 26(9):1633-1638.
Seidler et al. "Motor control and aging: links to age-related brain structural, functional, and biochemical effects", Neuroscience & Biobehavioral Reviews, (2010); 34(5):721-733, Oct. 2009.
Shibata et al. "Use of neuromelanin-sensitive MRI to distinguish schizophrenic and depressive patients and healthy individuals based on signal alterations in the substantia nigra and locus ceruleus", Biological Psychiatry, (Dec. 2008); 64(5):401-406.
Skinbjerg M, et al. "D2 dopamine receptor internalization prolongs the decrease of radioligand binding after amphetamine: a PET study in a receptor internalization-deficient mouse model", Neuroimage, (2010); 50(4):1402-1407, Jan. 2010.
Stolp et al. "Voxel-wise comparisons of cellular microstructure and diffusion-MRI in mouse hippocampus using 3D Bridging of optically-clear histology with Neuroimaging Data (3D-BOND)", Scientific Reports, (2018); 8(1):4011, 1-12, Mar. 2018.
Sulzer et al. "Neuromelanin biosynthesis is driven by excess cytosolic catecholamines not accumulated by synaptic vesicles", Proceedings of the National Academy of Sciences, (2000); 97(22):11869-11874, Aug. 2000.
Sulzer et al. "Neuromelanin detection by magnetic resonance imaging (MRI) and its promise as a biomarker for Parkinson's disease", NPJ Parkinson's Disease, (2018); 4(1):11, 13 pages, Apr. 2018.
Takahashi et al. "Detection of changes in the locus coeruleus in patients with mild cognitive impairment and Alzheimer's disease: High-resolution fast spin-echo T 1-weighted imaging", Geriatrics & Gerontology International, (Feb. 2014); 15(3):334-340.
Tanaka et al. "Neuromelanin-related contrast in the substantia nigra semiquantitatively evaluated by magnetic resonance imaging at 3T: comparison between normal aging and Parkinson disease", Rinsho Shinkeigaku= Clinical Neurology, (2011); 51(1):14-20, Dec. 2011.
Tavares et al. "Neuromelanin magnetic resonance imaging of the substantia nigra in first episode psychosis patients consumers of illicit substances", Schizophrenia Research, (2018); 197:620-621, Dec. 2018.
Trujillo et al. "Comparison of Neuromelanin MRI with FP-CIT SPECT in Parkinson Disease", Proc Intl Soc Mag Reson Med, (2014); 1920, 1 page, Dec. 2014.
Trujillo et al. "Contrast mechanisms associated with neuromelanin-MRI", Magnetic Resonance in Medicine, (Dec. 2016); 78(5):1790-800.
Vermeiren et al. "Brain region-specific monoaminergic correlates of neuropsychiatric symptoms in Alzheimer's disease", Journal of Alzheimer's Disease, (2014); 41(3):819-833, Feb. 2014.
Viceconte et al. "Neuromelanin activates proinflammatory microglia through a caspase-8-dependent mechanism", Journal of Neuroinflammation, (2015); 12:1-5, Jan. 2015.
Waehnert et al. "A subject-specific framework for in vivo myeloarchitectonic analysis using high resolution quantitative MRI", Neuroimage, (Oct. 2015); 125:94-107.
Wakamatsu et al. "Norepinephrine and its metabolites are involved in the synthesis of neuromelanin derived from the locus coeruleus", Journal of Neurochemistry, (2015); 135(4):768-776, Dec. 2015.
Wang et al. "Neuromelanin-sensitive MRI features of the substantia nigra and locus coeruleus in de novo Parkinson's disease and its phenotypes", Eur J Neurol., (2018); 25(7):949-e73, 22 pages, Dec. 2018.
Wang et al. "Neuromelanin-sensitive MRI of the substantia nigra: an imaging biomarker to differentiate essential tremor from tremor-dominant Parkinson's disease", Parkinsonism & Related Disorders, 58:3-8.
Watanab et al. "Neuromelanin magnetic resonance imaging reveals increased dopaminergic neuron activity in the substantia nigra of patients with schizophrenia", PLoS One, (2014); 9(8):e104619, 6 pages, Aug. 2014.
Wengler et al. "Reproducibility assessment of neuromelanin-sensitive magnetic resonance imaging protocols for region-of-interest and voxelwise analyses", Neuroimage, (2020); 208:116457, 43 pages, Dec. 2020.
Xiang et al. "Subtypes evaluation of motor dysfunction in Parkinson's disease using neuromelanin-sensitive magnetic resonance imaging", Neuroscience Letters, (Dec. 2016); 638:145-150.
Xing et al. "Life span pigmentation changes of the substantia nigra detected by neuromelanin-sensitive MRI", Movement Disorders, (2018); 33(11):1792-1799, Aug. 2018.
Yamashita et al. "Detection of changes in the ventral tegmental area of patients with schizophrenia using neuromelanin-sensitive MRI", Neuroreport, (2016); 27(5):289-294, Jan. 2016.
Zecca et al. "Human neuromelanin induces neuroinflammation and neurodegeneration in the rat substantia nigra: implications for Parkinson's disease", Acta Neuropathologica, (2008); 116:47-55.
Zecca et al. "Interaction of neuromelanin and iron in substantia nigra and other areas of human brain", Neuroscience, (1996); 73(2):407-415, Dec. 1996.
Zecca et al. "Neuromelanin can protect against iron-mediated oxidative damage in system modeling iron overload of brain aging and Parkinson's disease", Journal of Neurochemistry, (2008); 106(4):1866-1875, Dec. 2008.
Zecca et al. "The absolute concentration of nigral neuromelanin, assayed by a new sensitive method, increases throughout the life and is dramatically decreased in Parkinson's disease", FEBS Letters, (2002); 510(3):216-220, Jan. 2002.
Zecca et al. "Total and paramagnetic metals in human substantia nigra and its neuromelanin", Journal of Neural Transmission-Parkinson's Disease and Dementia Section, (Oct. 1992); 5:203-213.
Zhang et al. "Neuromelanin activates microglia and induces degeneration of dopaminergic neurons: implications for progression of Parkinson's disease", Neurotoxicity Research, (2011); 19:63-72, Jan. 2011.
Zucca et al. "Interactions of iron, dopamine and neuromelanin pathways in brain aging and Parkinson's disease", Progress in Neurobiology, (2017); 155:96-119, Aug. 2017.

(56) References Cited

OTHER PUBLICATIONS

Zucca et al. "Neuromelanin of the human substantia nigra: an update", Neurotoxicity Research, (Oct. 2013); 25:13-23.
Zucca et al. "Neuromelanin organelles are specialized autolysosomes that accumulate undegraded proteins and lipids in aging human brain and are likely involved in Parkinson's disease", NPJ Parkinson's Disease, (2018); 4(1):17, 23 pages, Jun. 2018.

* cited by examiner

SYSTEMS, DEVICES, AND METHODS FOR HARMONIZATION OF IMAGING DATASETS INCLUDING BIOMARKERS

CROSS-REFERENCE TO RELATED APPLICATIONS

This application claims priority to U.S. Provisional Application No. 63/159,915 entitled "CROSS-SCANNER HARMONIZATION OF NEUROMELANIN-SENSITIVE MRI FOR MULTISITE STUDIES," filed Mar. 11, 2021, the entire disclosure of which is incorporated herein by reference.

STATEMENT REGARDING FEDERALLY FUNDED RESEARCH

This invention was made with government support awarded by Grant Nos. R01-MH114965 and R01-MH117323 awarded by the National Institutes of Health. The government has certain rights in this invention.

FIELD OF INVENTION

The embodiments described herein relate to methods and apparatuses for generating and/or modifying data associated with Magnetic Resonance Imaging and, in particular, to providing harmonized data associated with multiple sources of Magnetic Resonance Imaging based on one or more biomarkers to improve accuracy in analyses based on the multiple sources of Magnetic Resonance Imaging.

BACKGROUND

The development and use of biomarkers is a promising approach to aid in the use of Magnetic Resonance Imaging techniques to probe biological systems. One example biomarker, Neuromelanin can be used as a pigment or an indicator to identify one or more biomarkers of neurodegeneration, for example in the dopaminergic system, via Neuromelanin-sensitive magnetic resonance imaging (NM-MRI). The development and use of biomarkers typically involves using large sample sizes of scan data obtained from several multi-site MRI studies conducted using different hardware and/or software. Combining scan data from multiple sites can introduce undesired variability into the data from differences in hardware and/or software. Thus, there exists a need for a method for combining imaging or scan data from multiple sites without introducing undue and undesired variability.

SUMMARY

In some embodiments, systems, devices, and methods described herein can assist scientists, physicians, researchers, clinicians, and other medical or clinical professionals in collecting and using large sets of imaging data across multiple sources to conduct robust studies and draw powerful inferences based on the Scan data. Embodiments include a method, comprising Embodiments disclosed include a method of harmonizing a dataset comprising measuring a first level of neuromelanin associated with a first Magnetic Resonance Imaging (MRI) machine. The method includes measuring a second level of neuromelanin associated with a second MRI machine. The method includes generating a set of input feature vectors based on the neuromelanin dataset. The method includes providing the set of input feature vectors to a machine learning model to adjust the first level of neuromelanin associated with the first MRI machine based on the second level of neuromelanin associated with the second MRI machine.

Embodiments disclosed include an apparatus, comprising a memory and a processor operatively coupled to the memory. The processor is configured to measure a set of first levels of neuromelanin at a set of timepoints using a first MRI machine. The processor is configured to measure a second level of neuromelanin using a second reference MRI machine different from the first MRI machine. The processor is configured to implement a machine learning (ComBat) algorithm to generate a scanner specific coefficient associated with the first MRI machine and the second reference MRI machine. The scanner specific coefficient is configured to define a relationship between the first MRI machine and the second reference MRI machine. The processor is configured to use the scanner specific coefficient to harmonize a set of data collected using the first MRI machine compared to the second reference MRI machine, the set of data including a number of NM scans.

Embodiments disclosed include a method of harmonizing a neuromelanin dataset using a vendor specific combat coefficient. The method comprises measuring a first level of neuromelanin associated with a first dataset obtained using a set of MRI machines manufactured by a first vendor, and measuring a second level of neuromelanin associated with second dataset obtained using a reference MRI machine manufactured by a second vendor different from the first vendor. The method includes implementing a machine learning (combat) algorithm to generate a vendor specific coefficient associated with the set of MRI machines, the vendor specific coefficient being based on at least one of (1) the first level of neuromelanin associated with a set of MRI machines or (2) the second level of neuromelanin associated with reference MRI machine. The method includes obtaining a third dataset associated with a first MRI machine manufactured by the first vendor. The method includes applying the vendor specific coefficient directly on the third dataset from the first MRI machine manufactured by the first vendor to measure an adjusted third level of neuromelanin associated with first MRI machine compared to at least one of (1) the second level of neuromelanin associated with the reference MRI machine or (2) the second dataset.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
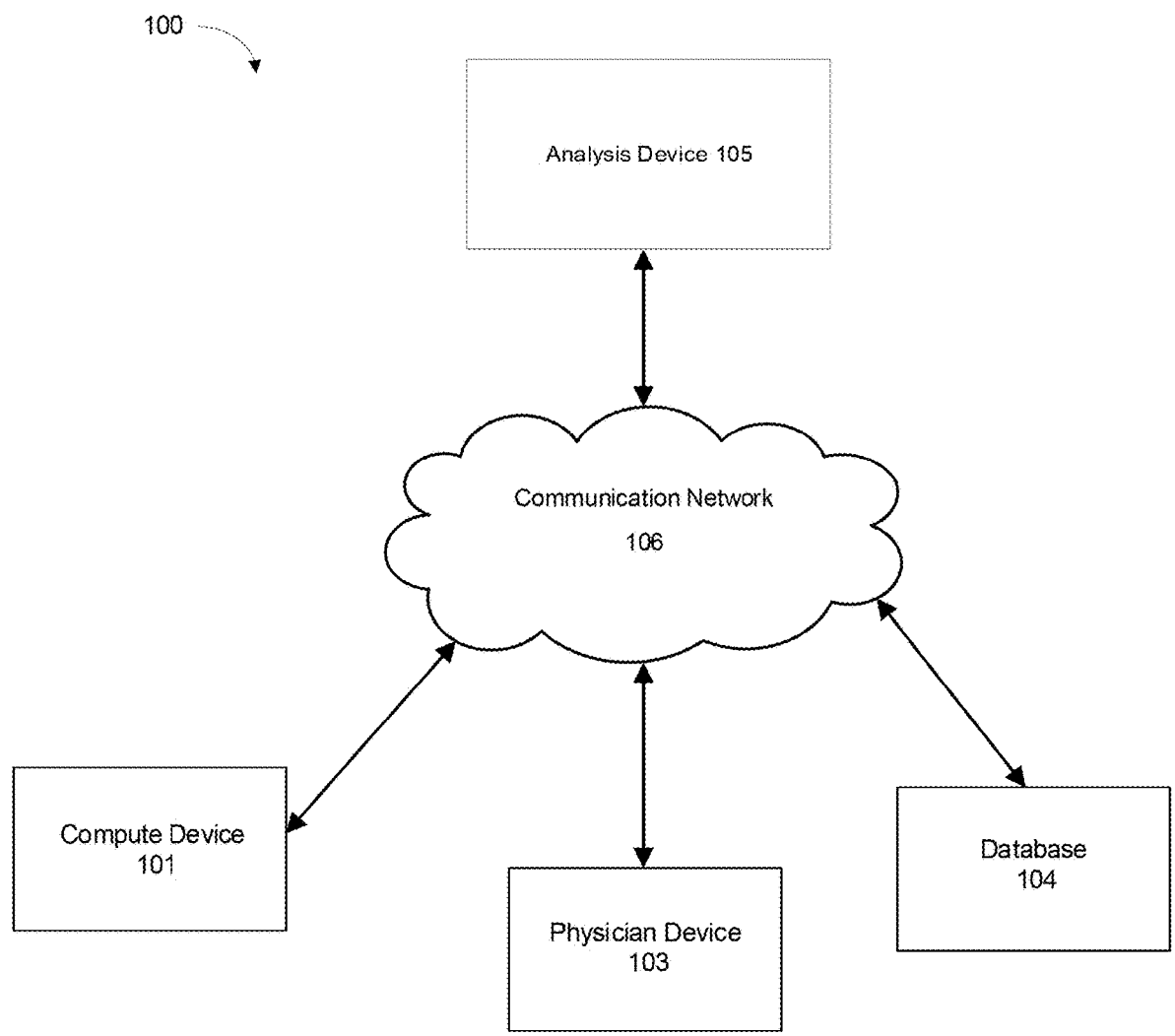
FIG. 1 is a schematic illustration of a Data Harmonization System (DH system), according to an embodiment.

Magnetic Resonance Imaging provides a non-invasive strategy of probing various biological systems for research and treatment. Image analysis can provide qualitative and/or quantitative information about the biological system based on one or more imaging biomarkers. An imaging biomarker can be an objective feature or characteristic that is consistently observed in an in vivo image, which can be reproducibly used as an indicator of a presence of a specified biological processes, pathogenic processes, or a response to an intervention (e.g., therapeutic manipulation), or the like. In some instances, a biomarker can be used to derive quantitative assessments of a biological tissue. For example, a biomarker can be measured on a relative scale, such as a ratio scale or an interval (difference) scale of two image values (e.g., intensities) that can be meaningfully interpreted. In some instances, biomarkers can be measured on an interval scale, A wide range of properties of biological tissue can be interrogated via MRI-based imaging by using biomarkers includes tissue microstructure, metabolism, composition, function, and morphology.

Biomarkers can be highly useful and of high demand, yet surprisingly few MRI biomarkers have been adopted for routine clinical use. The search for biomarkers in neuropsychiatric disorders is a major research agenda for the field and aligns with ongoing precision medicine initiatives.

Biomarkers can be targeted through biomarker specific imaging methods. Neuromelanin is one example of a biomarker or an indication of a biomarker that can be used extensively in research, diagnostic, clinical, and other medical efforts via Neuromelanin-sensitive magnetic resonance imaging (NM-MRI). NM-MRI has been shown to serve as a validated measure of neuromelanin concentration in the substantia nigra-ventral tegmental area complex (SN-VTA) and can be a proxy measure of dopaminergic function with excellent test-retest reliability. Given the importance of the dopaminergic system in both basic and clinical neuroscience, NM-MRI holds substantial potential as a noninvasive biomarker. The development of generalizable biomarkers typically requires large data samples collected across multiple studies and/or sites. As described, however, combining imaging data. e.g., NM-MRI data, obtained from multiple sources can introduce variability attributed to the sources that can lead the study astray.

Embodiments disclosed herein, include devices and methods to overcome challenges aced in large-scale integration of data from multiple studies/sites through harmonization of biomarker based MRI signals acquired from multiple sources. Examples disclosed herein show successful harmonization of NM-MRI data obtained from 128 healthy subjects from 3 different sites and obtained using 5 different MRI scanners. A machine learning algorithm (ComBat) was used to harmonize the imaging data, effectively reducing significant differences due to variability in SN-VTA NM-MRI signals across MRI scanners while preserving biologically meaningful variability associated with age effects. Harmonization also enhanced the reproducibility and statistical power of the known biologically meaningful age effects. The devices and methods presented here can be useful for large-scale multisite studies to develop NM-MRI-based biomarkers.

NM-MRI has been validated as a marker of both dopaminergic function and dopaminergic neurodegeneration, indicating potential for NM-MRI as a biomarker of the dopaminergic system. Furthermore, NM-MRI has several features positioning it as an ideal biomarker candidate: its noninvasive nature and lack of ionizing radiation allowing for repeated and longitudinal measurement, its ease of implementation, and its excellent test-retest reliability. The development and characterization of biomarkers typically involves using large sample sizes to facilitate training and testing of statistical models, and to provide generalizability. Multisite studies facilitate obtaining such large sample sizes, but a method for combining NM-MRI data from multiple sites has yet to be developed.

Combining imaging data from multiple sites can introduce unwanted, nonbiological variability into the data from differences in hardware (e.g., MRI scanner or head coil) or software (e.g., pulse sequence parameters). Including covariates in analyses (i.e., statistically controlling for site) does not sufficiently remove this variance and may preform no better than models which ignore the confounds.

Prior methods for harmonization of generalized data, that is, for the explicit removal of nonbiological variability include a machine learning algorithm called ComBat, which has emerged as a standard literature standard. The ComBat algorithm is an empirical Bayesian method for harmonizing both the mean and variance across batches of data and is particularly robust for handling small sample sizes of data sets. The approach of using ComBat algorithm was previously applied to MRI based measurement of cortical thickness, regional brain volumes and cortical surface area, diffusion tensor imaging, resting-state functional MRI, and task-based functional MRI There are, however, no established methods to apply the ComBat algorithm to biomarker specific imaging data sets. For example, there is an unmet need for a method of applying the ComBat algorithm to harmonization of neuromelanin specific imaging data obtained via NM-MRI.

Systems, devices, and methods disclosed herein can implement a method for harmonization of biomarker specific imaging data from multiple MRI sources across multiple imaging sessions, where acquisition parameters were not optimized across the imaging sessions. For example, systems, devices, and methods disclosed herein can implement a method for harmonization of NM-MRI data obtained from multiple patients, imaged across multiple sites, imaged using multiple MRI machines, and/or imaged using multiple MRI machines of multiple vendors like GE, Siemens, and Philips, where acquisition parameters were not optimized across the various imaging sessions. Systems, devices, and methods disclosed herein can implement a method for harmonization of NM-MRI data while maintaining biologically meaningful variability, for example variability associated with age. Examples presented herein show a successful harmonization of the NM-MRI data obtained from 3 major MRI vendors (GE, Siemens, and Philips) while maintaining biologically meaningful variability associated with increased NM-MRI signal with age. Examples also show and that harmonization improved both the reproducibility and statistical power of the expected positive relationship between the NM-MRI signal and age.

FIG. 1 is a schematic illustration of a system 100, which can be Data Harmonization system (also referred to herein as "an DH system" or "a system"). The system 100 includes a set of compute devices, including, for example, an analysis device 105 (e.g., an analysis device configured for data harmonization), a database 104 (e.g., a database containing or storing specified MRI images associated with one or more biomarkers, one or more patients, one or more vendors of MRI equipment, etc.), and one or more other compute device(s) 101, 103. The system 100 can aid in harmonization of biomarker specific imaging data provided by users (e.g., physicians, radiologists, diagnosticians, clinicians, research specialists, etc.) and/or computer-assisted diagnostic devices. The analysis device 105, physician device 103, and/or compute device(s) 101 can communicate with one another through a communications network 106, as illustrated in FIG. 1.

The analysis device 105 can receive biomarker specific imaging data associated with one or more sources from any suitable device (e.g., compute device 101 or physician device 103) or database (e.g., database 104) and a request to harmonize the data, with a standard reference or with each other if including data from multiple sources. The imaging data can include images obtained via biomarker specific MRI (e.g., NM-MRI) as well as information associated with the source (e.g., identity of the device sending the request for harmonization, identity of imaging source associated with the imaging data including patient, time of imaging each data set, site of imaging associate with each data set, equipment used, acquisition parameters used in each imaging session, etc.,). The analysis device 105 can preprocess the imaging data and/or implement an algorithm (e.g., ComBat algorithm) to harmonize the imaging data as requested. The harmonized imaging data can be provided to a device, for example the compute device(s) 101 and/or physician device 103 in the same format or in a suitably modified format, according to an embodiment.

In some embodiments, the communication network 106 (also referred to as "the network") can be any suitable communications network for transferring data, operating over public and/or private networks. For example, the network 106 can include a private network, a Virtual Private Network (VPN), a Multiprotocol Label Switching (MPLS) circuit, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof. In some instances, the communication network 106 can be a wireless network such as, for example, a Wi-Fi or wireless local area network ("WLAN"), a wireless wide area network ("WWAN"), and/or a cellular network. In other instances, the communication network 106 can be a wired network such as, for example, an Ethernet network, a digital subscription line ("DSL") network, a broadband network, and/or a fiber-optic network. In some instances, the network can use Application Programming Interfaces (APIs) and/or data interchange formats, (e.g., Representational State Transfer (REST), JavaScript Object Notation (JSON), Extensible Markup Language (XML), Simple Object Access Protocol (SOAP), and/or Java Message Service (JMS)). The communications sent via the network 106 can be encrypted or unencrypted. In some instances, the communication network 106 can include multiple networks or subnetworks operatively coupled to one another by, for example, network bridges, routers, switches, gateways and/or the like (not shown).

The compute devices in system 100, including, for example, analysis device 105, physician device 103, and/or other compute device(s) 101 can each be any suitable hardware-based computing device and/or a multimedia device, such as, for example, a server, a desktop compute device, a smartphone, a tablet, a wearable device, a laptop and/or the like. The physician device 103 can be, for example, a workstation or other device such as an MRI scanner that is used by a physician, radiologist, diagnostician, researcher or other individual associated with an imaging data set. For example, in some embodiments, the physician device 103 can include a radiology workstation associated with a radiologist and/or a radiological service providing entity. In some instances, the radiology workstation can be equipped to obtain radiological imaging data of samples from patients and/or medical institutions and communicate with the system 100 such that the scanned imaging data may be transmitted to the analysis device 105, the database 104, and/or other compute device(s) 101. In some instances, the imaging data can be suitably updated (e.g., annotated), and/or transmitted from the radiology workstation via a DICOM viewer application. In some instances, the imaging data can be suitably updated (e.g., annotated), and/or transmitted from the radiology workstation via a DICOM viewer application. Other compute device(s) 101 can include other devices that are part of a data harmonization system, including, for example, computational systems (e.g., systems including devices implementing computational algorithm, systems providing computational services such as cloud based computational frameworks, etc.) workstations, servers, user or patient devices, and/or the like.

The system 100 can also include a database 104, e.g., for storing data associated with patients, hospitals, imaging systems, etc. In some instances, the database 104 can include one or more devices that may be a part of a Picture Archival and Communication System (PACS), for example a PACS server. Devices part of a PACS system, such as a PACS server, can be configured for digital storage, transmission, and retrieval of medical images such as radiology images. A PACS server may include software and/or hardware components which directly interface with imaging modalities. The images may be transferred from the PACS server to one or more compute device(s) 101 (e.g., CAD devices) for viewing and/or reporting, and/or to the analysis device 105 for analysis. In some instances, a compute device 101 (e.g., a CAD device) may access images from the database 104 (e.g., a PACS server) and send it to the analysis device 105. In some instances, a compute device 101 (e.g., a CAD device) may obtain images directly from a physician device 103 (e.g., a radiology workstation) and send it to the analysis device 105.

Figure 2:
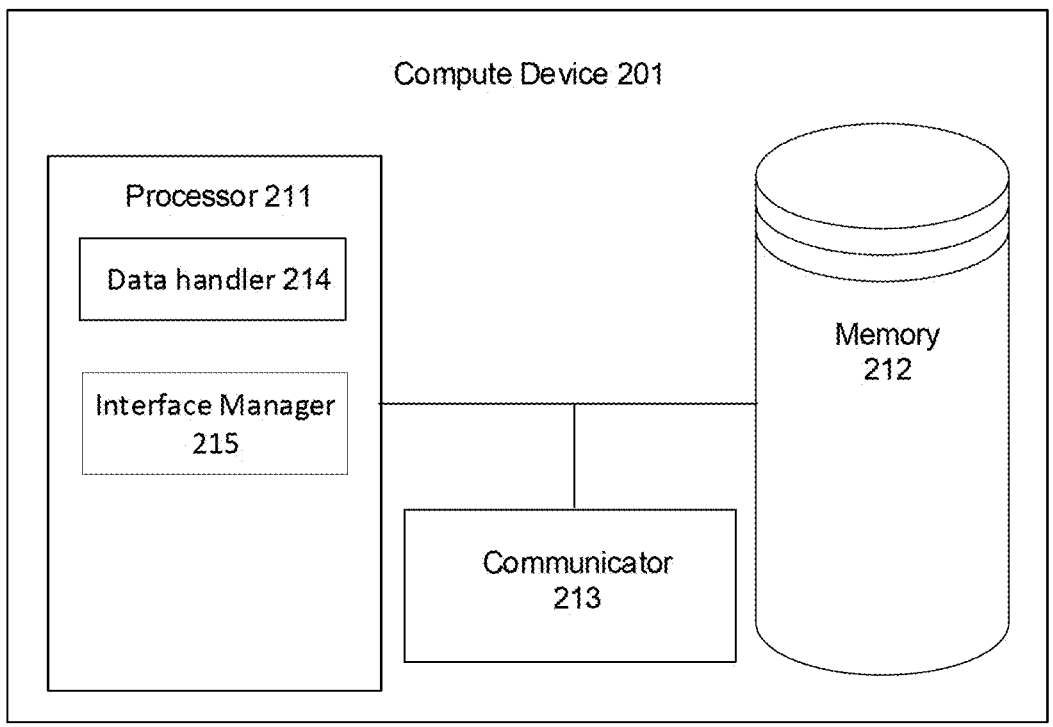
FIG. 2 is a schematic representation of a compute device within a data harmonization system, according to an embodiment.

FIG. 2 is a schematic block diagram of an example compute device 201 that can be a part of a data harmonization system (e.g., system 100), according to an embodiment. The compute device 201 can be structurally and/or functionally similar to the compute device(s) 101 and/or physician device 103 of the system 100 illustrated in FIG. 1. The compute device 201 can be a hardware-based computing device and/or a multimedia device, such as, for example, a server, a desktop compute device, a smartphone, a tablet, a wearable device, a laptop, an ultrasound scanner, and/or the like. The compute device 201 includes a processor 211, a memory 212 (e.g., including data storage), and a communicator 213. In some embodiments, the compute device 201 can have any suitable number of additional components (not shown) including input/output devices, display devices, and the like.

The processor 211 can be, for example, a hardware based integrated circuit (IC) or any other suitable processing device configured to run and/or execute a set of instructions or code. For example, the processor 211 can be a general-purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 211 can be operatively coupled to the memory 212 through a system bus (for example, address bus, data bus and/or control bus). As described herein, the compute device 201 can be associated and/or operatively coupled to an imaging machine (e.g., an MRI machine) and configured to obtain imaging data acquired by the machine over one or more imaging sessions based on specified image acquisition parameters set on the imaging machine.

The processor 211 can be configured to receive and/or obtain imaging data, meta data, clinical information, medical information, other information, etc. from a remote source (e.g., a clinical database (e.g., database 104), repository, scanner, imaging device, other device associated with a radiological service, devices associated with a patient management system/hospital, devices associated with individuals/patients, etc.). In some instances, the processor 211 can be configured to receive imaging data and/or data associated with imaging data (e.g., processed data, measurements associated with the imaging data, annotations associated with the imaging data, biographical/clinical data associated with imaging data, etc.) from any suitable source including an imaging (e.g., MRI machine), workstation, physician's device, patient device, database, or any other suitable device.

The processor 211 can receive commands to handle the data (e.g., receive command to harmonize the data). In some instances, the processor 211 can implement a user interface at the compute device 201, as described in further detail herein, to receive commands for example from a user. For example, the processor 211 can be configured to cause an input/output device (e.g., an input/output device coupled to communicator 213 or integrated into compute device 201) to display an interface to an operator (e.g., a physician).

The processor 211 can pre-process, organize, and or initiate harmonization of the data, in response to one or more commands. In some instances, the processor 211 at the compute device 201 can be configured to automatically identify a source of a data or determine a lack of identified source of a data.

In some instances, the processor 211 can preprocess the data and sent it to an analysis device to initiate harmonization of the data, as described herein. In some instances, the processor 211 can be configured to receive harmonized data and in some embodiments, confirm a state of harmonization of a dataset. The processor 211 can be configured to present to a user information associated with an imaging data set (e.g., information indicating a measure of harmonization or information indicating a retention of biological variability, or the like).

The processor 211 can include or execute one or more module(s) or instruction(s) stored in memory 212 to function as a data handler 214, and an interface manager 215. In some embodiments, the processor 211 can include software applications (not shown in FIG. 2) that can be used to provide an interface to deliver diagnostic assessments. The software application can be any suitable software or code that when executed by the processor 211 can be configured to perform a group of coordinated functions, tasks, or activities for the benefit of a user of the compute device 201. Software application can be, for example, browser applications, word processing applications, media playing applications, JAVA based applications, image rendering or editing applications, text editing applications, and/or the like.

In some embodiments, each of the data handler 214, and the interface manager 215, and/or the software applications can be software stored in the memory 212 and executed by the processor 211. For example, each of the above-mentioned portions of the processor 211 can be implemented in the form of instructions that can include code that is configured to cause the processor 211 to execute the data handler 214, and the interface manager 215, and/or the software applications. The code can be stored in the memory 212 and/or a hardware-based device such as, for example, an ASIC, an FPGA, a CPLD, a PLA, a PLC and/or the like. In other embodiments, each of the data handler 214, the and interface manager 215, and/or the software applications can be hardware configured to perform their respective functions.

The processor 211 implementing data handler 214 can be configured to collect imaging data, annotation data, clinical data, and/or any other associated data related to patients, sites, imaging sessions, scanning equipment, medical/clinical institutions, and/or imaging studies conducted and/or the like. For example, the data handler 214 can receive, collect, process, and/or store imaging data such as radiological data provided for a study, diagnosis, or evaluation of a biological system in a subject.

The imaging data can be in the form of a plurality of images. In some instances, the plurality of images can be acquired in a spatial sequence (e.g., in successive spatial locations of a biological tissue following a spatial order). In some instances, the plurality of images can be acquired in a temporal sequence (e.g., in successive temporal windows imaging a biological tissue following a temporal order). In some instances, the plurality of images can be acquired in a spatiotemporal sequence having a spatiotemporal order. The imaging data can also include meta data or supplemental details in any suitable form associated with the imaging data providing additional information associated with the circumstances of acquiring the imaging data. For example, the additional imaging machine and/or the patient imaged. For example, the imaging data can include meta data or supplemental details in the form of information associated with the image acquisition parameters, information associated with the equipment used (vendor details of the imaging machine such as make, model, data and batch of manufacture etc.), information associated with calibration of the machine, etc. In some instances, the imaging data can be in the form of images obtained from a biomarker specific MRI (e.g., NM-MRI). In some instances, the imaging data can be in the form of DICOM images and associated meta-data.

The data handler 214 can also obtain clinical, annotation based, or otherwise supplemental data associated with the imaging data. one or more patient(s), image sites, imaging windows (i.e., time/date of imaging), biological conditions, etc. to organize the data. In some instances, the clinical data can include, for example, histopathological data associated with the biological tissue imaged, medical information, biographic information associated with the subject or patient, information about other details of the patient including age, gender, ethnicity, health, history, etc. In some instances, the data handler 214 can determine a lack of a specified information (e.g., lack of an identity of a scanner associated with a dataset) and await a user input via an interface, for example implemented by an interface manager 215, to provide the information regarding the identity of a scanner associated with a dataset. In some implementations, the data handler 214 and/or the interface manager 215 can also prompt a user to provide one or more specified inputs to record the information associated with an imaging data set. In some implementations the imaging data can be suitably encrypted, for example, to protect private data associated with patients, subjects, organizations, clinical studies, etc. In some implementations, the data handler 214 can be configured to decrypt encrypted data as needed to extract information associated with the imaging dataset. The data handler 214 can also be configured to suitably encrypt information before sending the information to another device (e.g., an analysis device, database, compute device, etc.)

In some implementations, the data handler 214 can be configured to evaluate an identified imaging data to determine if it has been harmonized or not. In some instances, the data handler 214 can be configured to receive a query, for example from a user via an interface managed by the interface manager 215, and in response to the query evaluate whether an identified imaging data set is harmonized. In some implementations, the data handler 214 can be configured to automatically evaluate an identified imaging data to determine if it has been harmonized or not, for example, by comparing the identified imaging data with a predetermined reference imaging dataset.

In some implementations, the processor 211 implementing the data handler 214 can be configured to receive instructions from an operator or physician via an interface (e.g., a user interface implemented and managed, for example, by the interface manager 215) to harmonize one or more datasets according a predetermined condition. The data handler 214 can organize the data needed to harmonize the one or more datasets according the predetermined condition and provide the data to an analysis device (e.g., analysis device 105 of FIG. 1). In some embodiments, the processor 211 can implement data handler 214 as a background process that monitors for newly incoming data, processes that data, and/or stores that data.

The interface manger 215 can be configured to provide an interface (also referred to herein as "user interface") to an operator of the compute device 201, through which the operator may load or access imaging data or any associated supplemental data, evaluate the imaging data or the supplemental data and/or initiate harmonization of the data. In some implementations, the interface manager 215 can provide control options to a user, via an interface, for example, to modify and/or customize settings in an interface to organize imaging and/or supplemental data assigning or organizing a data structure to the imaging data and/or supplemental data. In some implementations, the interface manager 215 can be configured to provide control tools for the operator or user to add supplemental information that may not already be associated with the imaging data. For example, the interface manager 215 can provide for a user to input information related to the source of an imaging dataset (e.g., information related to biographic or demographic information about a patient, time of imaging, site of imaging, imaging equipment, etc.). In some instances, the interface manager 215 can be configured to provide tools for a user to initiate a harmonization of an imaging data set, as described herein. For example, the interface manager 215 can receive instructions from a user to initiate harmonization of an imaging data set and in response to the instructions, send a signal to an analysis device (e.g., analysis device 105, 205 described herein) to perform the harmonization.

The interface manager 215 can be configured to receive harmonized imaging data, for example from an analysis device (e.g., analysis device 105, 205) and provide the harmonized imaging data for further processing, study, analysis, evaluation, storage, and/or the like.

While described herein as performed by a compute device 201 that can be separate from an analysis device that performs harmonization of a data set, the compute device 201 implementing the data handler 214 and the interface manager 215, in some embodiments, can be the same analysis device that performs the harmonization of a data set. In other words, one or more of the above-described processes described with respect to the processor 211, e.g., implementing the data handler 214 and/or the interface manager 215, can be performed by an analysis device (e.g., analysis device 105 that is included in the system 100 shown in FIG. 1, and/or the analysis device 305 shown in FIG. 3 and described in further detail in the following sections).

While the compute device 201 is described to implement, via the processor 211, each of a data handler 214 and the interface manager 215, it can be appreciated that a compute device can be configured with several instances of the above-mentioned units, components, and/or modules. Moreover, the terms data handler and interface manager are provided for illustrative purposes, e.g., to explain the processes implemented by the processor 211. Therefore, one or more of these modules can be combined into single modules or generally referred to as a processor configured to perform one or more processes or steps thereof.

The memory 212 of the compute device 201 can be, for example, a random-access memory (RAM), a memory buffer, a hard drive, a read-only memory (ROM), an erasable programmable read-only memory (EPROM), and/or the like. The memory 212 can store, for example, one or more software modules and/or code that can include instructions to cause the processor 211 to perform one or more processes, functions, and/or the like (e.g., the data handler 214, the interface manger 215, and/or the software applications described above). In some embodiments, the memory 212 can include extendable storage units that can be added and used incrementally. In some implementations, the memory 212 can be a portable memory (for example, a flash drive, a portable hard disk, and/or the like) that can be operatively coupled to the processor 211. In other instances, the memory can be remotely operatively coupled with the compute device. For example, a remote database server can serve as a memory and be operatively coupled to the compute device.

The communicator 213 can be a hardware device operatively coupled to the processor 211 and memory 212 and/or software stored in the memory 212 executed by the processor 211. The communicator 213 can be, for example, a network interface card (NIC), a Wi-Fi™ module, a Bluetooth® module and/or any other suitable wired and/or wireless communication device. Furthermore, the communicator 213 can include a switch, a router, a hub and/or any other network device. The communicator 213 can be configured to connect the compute device 201 to a communication network (such as the communication network 106 shown in FIG. 1). In some instances, the communicator 213 can be configured to connect to a communication network such as, for example, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof.

In some instances, the communicator 213 can facilitate receiving and/or transmitting signals (e.g., signals to initiate harmonization of a data set), data (e.g., imaging data, supplemental data, clinical data, etc.), a file and/or a set of files through a communication network (e.g., the communication network 106 in the system 100 of FIG. 1). In some instances, a received file can be processed by the processor 211 and/or stored in the memory 212 as described in further detail herein. In some instances, as described previously, the communicator 213 can be configured to send data collected and/or analyzed by the data handler 214 to an analysis device (e.g., analysis device 105) of a data harmonization system (e.g., system 100) to which the compute device 201 is connected. The communicator 213 can also be configured to send data collected and analyzed by the data handler 214 and the results of any analyses generated, to the analysis device of a data harmonization system to which the compute device 201 is connected.

Figure 3:
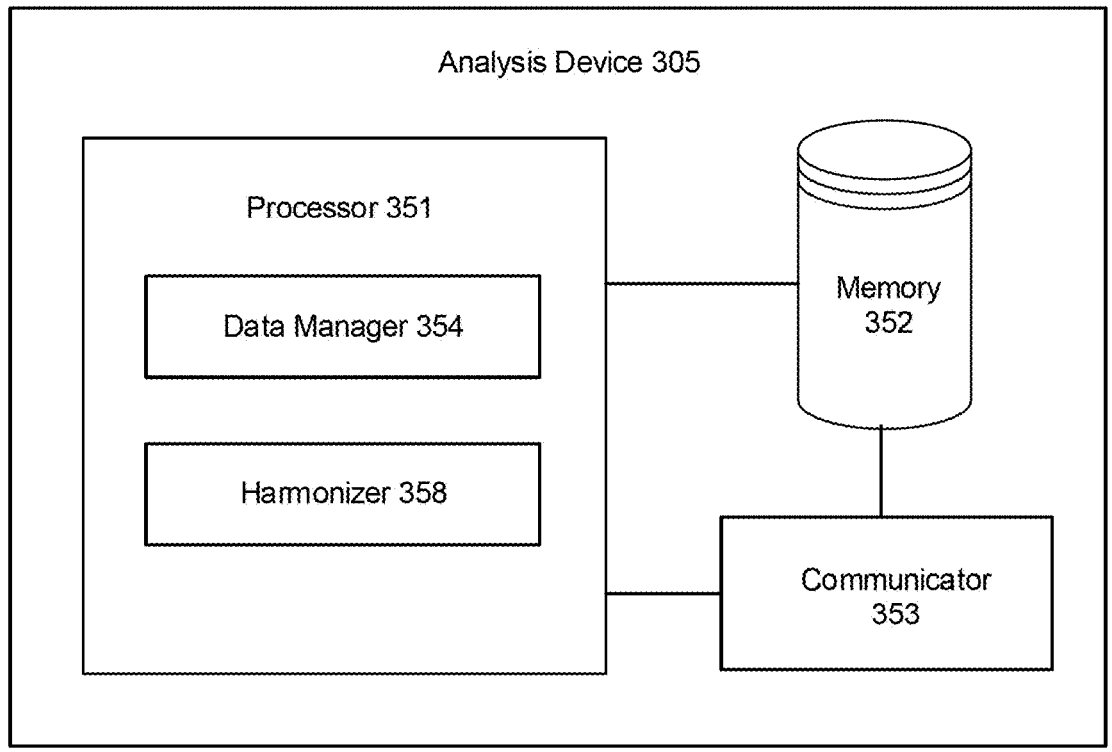
FIG. 3 is a schematic representation of an analysis device within a data harmonization system, according to an embodiment.

Returning to FIG. 1, the compute device 101 that is connected to the system 100 can be configured to communicate with the analysis device 105 via the communication network 106. FIG. 3 is a schematic representation of an analysis device 305 that is part of a data harmonization system (e.g., system 100), according to some embodiments. The analysis device 305 can be structurally and/or functionally similar to the analysis device 105 of the system 100 illustrated in FIG. 1. The analysis device 305 includes a communicator 353, a memory 352, and a processor 351.

Similar to the communicator 213 within compute device 201 of FIG. 2, the communicator 353 can be a hardware device operatively coupled to the processor 351 and the memory 352 and/or software stored in the memory 352 executed by the processor 351. The communicator 353 can be, for example, a network interface card (NIC), a Wi-Fi™ module, a Bluetooth® module and/or any other suitable wired and/or wireless communication device. Furthermore, the communicator 353 can include a switch, a router, a hub and/or any other network device. The communicator 353 can be configured to connect the analysis device 305 to a communication network (such as the communication network 106 shown in FIG. 1). In some instances, the communicator 353 can be configured to connect to a communication network such as, for example, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof.

The memory 352 can be a random access memory (RAM), a memory buffer, a hard drive, a read-only memory (ROM), an erasable programmable read-only memory (EPROM), and/or the like. The memory 352 can store data, for example, imaging data and/or any supplemental data associated with imaging data. The memory 352 can store, for example, one or more software modules and/or code that can include instructions to cause the processor 351 to perform one or more processes, functions, and/or the like. In some implementations, the memory 352 can be a portable memory (e.g., a flash drive, a portable hard disk, and/or the like) that can be operatively coupled to the processor 351. In other instances, the memory 352 can be remotely operatively coupled with the analysis device 305. For example, the memory can be a remote database server operatively coupled to the analysis device 305 and its components and/or modules.

The processor 351 can be a hardware based integrated circuit (IC) or any other suitable processing device configured to run and/or execute a set of instructions or code. For example, the processor 351 can be a general-purpose processor, a central processing unit (CPU), a graphics processing unit (GPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 351 is operatively coupled to the memory 352 through a system bus (e.g., address bus, data bus and/or control bus). The processor 351 is operatively coupled with the communicator 353 through a suitable connection or device as described in further detail.

The processor 351 can be configured to include and/or execute several components, units and/or modules that may be configured to perform several functions, as described in further detail herein. The components can be hardware-based components (e.g., an integrated circuit (IC) or any other suitable processing device configured to run and/or execute a set of instructions or code) or software-based components (executed by the server processor 352), or a combination of the two.

As illustrated in FIG. 3, the processor 351 includes or can execute one or more module(s) or instruction(s) stored in the memory 352 to function as a data manager 354 and a harmonizer 358.

The data manager 354 in the processor 351 can be configured to receive communications between the analysis device 305 and compute devices connected to the analysis device 305 through suitable communication networks (e.g., compute devices 101-103 connected to the analysis device 105 via the communication network 106 in the system 100 in FIG. 1). The data manager 354 is configured to receive, from the compute devices, data bases, and/or from remote sources, information pertaining to imaging data (e.g., biomarker specific MRI data like NM-MRI datasets), supplemental data such as clinical data, biographic data, annotations, etc. In some implementations, the data manager 354 can receive data from compute devices via signals sent through an interface (e.g., a user interface implemented by an interface manager such as interface manager 215).

The data manager 354 can be configured to receive radiological imaging data from physicians, researchers, patients, and any other suitable users, the data being associated with organs and/or organ systems under clinical or therapeutic analysis or study. In some instances, the data manager 354 can receive information associated with medical history of patients, biographical information (e.g., age, gender, race, ethnicity, health history, behavioral habits, etc.). The data manager 354 can receive information associated with a reference data set that can be used to harmonize any given imaging data set by reducing variability in the given data set. The imaging data and/or the reference data can be in the form of DICOM images and associated meta-data, or other imaging data. In some implementations the imaging data and/or the reference data can be suitably encrypted, for example, to protect private data associated with patients, subjects, organizations, clinical studies, etc. In some implementations, the data manager 354 can be configured to decrypt encrypted data as needed to extract information associated with the imaging dataset. The data manager 354 can also be configured to suitably encrypt information before sending the information to another device (e.g., a portal device, database, compute device, etc.)

In some instances, the processor can include one or more machine learning models (not shown in FIG. 3) configured to receive information associated with an identified imaging data, for example, in the form of feature vectors extracted by the data manager 354. Models may include, but are not limited to, deep neural networks, multi-layer perceptrons, random forests, support vector machines, etc. The machine learning models can be configured to process the information to provide outputs, e.g., in the form of coefficients configured to reduce variability. In some instances, the processor can be configured to harmonize data obtained from a first source (e.g., imaging data obtained using a first equipment, from a first subject and/or at a first time point) with data obtained from a second source (e.g., imaging data obtained using a second equipment, from a second subject, and/or at a second time point). The coefficients can be configured to define a relationship between the first source and the second source. In some instances, the second source can be a reference source used to harmonize multiple datasets. In some embodiments, the machine learning models can be configured to provide outputs that include one or more coefficients, functions (e.g., transformation functions), etc. for harmonizing data from different sources.

The machine learning models can be configured to process the information to provide outputs indicating one or more classes associated with the imaging data. For example, the machine learning models can serve as classifiers and process the information associated with the imaging data to provide as output a classification of a source of non-biological variability in the imaging data (e.g., a class of imaging equipment defined by manufacturer, model, etc. used to generate the data). The model can in some implementations, be used to provide an output indicating a classification of a source of biologically or biographically meaningful variability in the imaging data (e.g., a classification based on age, gender, race, and/or the like). In some implementations, the machine learning model can be used to evaluate before and/or after normalizing or harmonization of an imaging data set.

The processor 351 includes a harmonizer 356 configured to implement a routine or algorithm (e.g., ComBat Algorithm configured to harmonize NM-MRI imaging data sets) to harmonize an identified imaging dataset by reducing or decreasing sources of non-biologically or non-biographically meaningful variability associated with the identified data set. Harmonization can include identifying one or more sources of non-biological variability (e.g., variability associated with imaging equipment) and defining one or more coefficients, which when applied to an identified imaging dataset can be configured to reduce the amount of non-biological variability associated with the dataset. The harmonizer 358 can be configured to receive an identified dataset and any supplemental data associated with the identified imaging data set. The harmonizer 358 can evaluate the supplemental data to determine a source of undesired variability associated with the identified imaging dataset. In some implementations, the source of undesired variability can be a source of non-biological variability. For example, the supplemental data can indicate a source associated with the imaging data set. The source can be an identified imaging equipment (e.g., an identified scanner or MRI machine), an identified manufacture or model of imaging or scanning equipment (e.g., a manufacturer of MR machines like GE, Phillips, Siemens, etc.), an identified patient, etc. In some implementations, the biological sources of variability may be the focus of study (e.g., variability in biomarker specific MRI associated with age, gender, race, etc.). In such studies, reducing the non-biological sources of variability (e.g., derived from variations in MRI scanners, image acquisition parameters, or scanner manufacturers, etc.) may be of value to accurately identify the variability that is due to the biological differences associated with samples, patients, and/or imaging datasets. The harmonizer 358 can be configured to run a machine learning algorithm (e.g., ComBat algorithm) to define one or more coefficients (e.g., ComBat coefficients), which when applied to adjusting or transforming an imaging data set, can generate a normalized or harmonized dataset with reduced variability from the undesired non-biological sources, while retaining the variability associated with the desired biological sources.

In some implementations, the source of undesired variability can be of biological origin but not the source that is under study at a particular instance. For example, one source of variability that may be of biological origin can be the focus of a study (e.g., age) while a second source of variability that may be of biological origin (e.g., gender) can be undesired and to be controlled in that given study. The harmonizer 358 can be configured to define coefficients configured to reduce the variability from undesired sources. The harmonizer 358 can be configured to define coefficients configured that when applied to an identified imaging dataset can generate a harmonized dataset with reduced variability associated with the undesired biological sources, while retaining the variability associated with the desired biological sources.

The harmonizer 358 can receive a reference imaging data set and be configured to generate coefficients for an identified imaging data set based on the reference imaging data set such that the identified imaging data, when applying the coefficients, can be harmonized with respect to the reference imaging data set. The reference imaging dataset can be chosen based on the variability that is to be reduced through the harmonization procedure.

In some implementations, the harmonizer 358 can generate coefficients using the raw imaging data. In some implementations, the harmonizer 358 can generate coefficients using processed data based on the imaging data. For example, the harmonizer 358 can use preprocessed data that has been averaged, registered, realigned, and/or transformed in any suitable format, for example, to be consistent with a reference image. In some implementations, the harmonizer 358 can use one or more masks over predetermined regions of the imaging data to obtain one or more measures associated with a biomarker. The harmonizer 358 can then run the algorithm (e.g., ComBat algorithm) over the measures to generate the coefficients. The measures can be calculate using any suitable process.

In some example implementations of the systems and methods described herein, MRI datasets obtained using a variety of scanner across a variety of clinical studies can be standardized to allow meaningful comparisons one-to-one between the datasets. In some embodiments the harmonizer 358 can be configured to standardize biomarker measurements in different subjects measured on different MRI machines or with varying parameters of image acquisition. For example, the harmonizer 358 can be configured to standardize NM measurements in different subjects measured on different MRI machines or the same MRI machine with different parameters. In some embodiments, the measurements can be collected in the setting of a large clinical trial. Datasets from different MRI machines would not be initially comparable as parameters between MRI machines are not optimized or designed to be consistent with one another. After all of the patients have completed a clinical study, the data harmonization systems and methods described herein can be implemented by, for example, running the ComBat algorithm over all biomarker specific measures (e.g., the CNR-NM voxels within a mask region of each patient). Implementing combat algorithm adjusts the differences in noise generated due to MRI scanner variability between each CNR-NM voxel and standardizes each CNR-NM voxel measurement against a reference standard MRI machine.

The harmonizer 358 can run the ComBat algorithm on a database of measures derived from voxels of the imaging data, as described herein. First, an NM sensitive MRI can be performed on a subject resulting in a raw brain MRI image. After preprocessing, a mask is applied to an identified brain region, for example the Substantia Nigra-Ventral Tegmental Area (SN-VTA) region of the image. A measure, for example a contrast to noise ratio (CNR) is calculated between voxels within the mask in the SN-VTA region and voxels in a control region of the image data. The processed voxels are referred to as CNR-NM voxels. These CNR-NM voxels from each patient who participates in the clinical trial are stored in a database. This database may contain data from multiple patients who have received an NM-MRI scan on different MRI machines.

In some example implementations, the input into ComBat algorithm can be CNR-NM voxels and the output generated by ComBat algorithm can be referred to as ComBat harmonized contrast to noise ratio neuromelanin voxels CH-CNR-NM voxels. The CH-CNR-NM voxels are then stored in the database for each individual patient. This implementation allows standardization of a large database that includes CNR-NM voxels measured on different MRI machines or the same MRI machine with different parameters by running combat algorithm once at the end of a clinical trial. In such an example implementation, NM voxels that have not been processed into CNR-NM voxels can be not a suitable input into combat and running combat algorithm on NM voxels alone may not provide the desired output.

For example, preprocessed NM-MRI images in a MNI template (an established template) space can be used to estimate NM-MRI contrast ratio (CNR) maps. NM-MRI CNR at each voxel can be calculated as a percent signal difference in NM-MRI signal intensity at a given voxel ($I_V$) from the signal intensity in the crus cerebri ($I_{CC}$)—a region of white matter tracts known to have minimal NM content—as:

$CNR_V = \{[I_V - \text{mode}(I_{CC})]/\text{mode}(I_{CC})\} \times 100$, where mode ($I_{CC}$) is calculated for each participant from a kernel-smoothing-function fit to a histogram of all voxels in the CC mask following our prior work.

CNR values of the voxels in the substantia nigra-ventral tegmental area complex (SN-VTA) mask can then harmonized using the ComBat harmonization model to remove nonbiological variability (associated with variations in the MRI scanning equipment) while maintaining biological variability (e.g., variability associated with age and gender). Other examples can include harmonizing outcome measures (e.g., SN-VTA CNR or regional brain volumes) instead of the raw MRI signal. The model can be written as:

$$y_{ijv} = \alpha_v + X_{ij}^T \beta_v + \gamma_{iv} + \delta_{iv} \varepsilon_{ijv}$$

where $y_{ijv}$ is the CNR value of MRI scanner i (i∈{1, ..., 5}), subject j (j∈{1, ..., 128}), and SN-VTA voxel v (v∈{1, ..., 1807}); $\alpha_v$ is the average CNR value for SN-VTA voxel v; X is a design matrix for the covariates of interest (age and gender); $\beta_v$ is a vector of regression coefficients corresponding to X for SN-VTA voxel v; $\gamma_{iv}$ and $\delta_{iv}$ are the additive and multiplicative effects of MRI scanner i for SN-VTA voxel v, respectively; and $\varepsilon_{ijv}$ are the error terms that are assumed to follow a normal distribution with mean 0 and variance $\sigma_v^2$.

The ComBat-harmonized CNR values can be defined as:

$$y_{ijv}^{ComBat} = \frac{y_{ijv} - \widehat{\alpha_v} - X_{ij}\widehat{\beta_v} - \gamma_{iv}^*}{\widehat{\delta_{iv}^*}} + \widehat{\alpha_v} + X_{ij}$$

where $\gamma_{iv}^*$ and $\delta_{iv}^*$ are the empirical Bayes estimates of $\gamma_{iv}$ and $\delta_{iv}$, respectively. Harmonization of the SN-VTA CNR can, in some instances, be performed using pre-available computational packages (e.g., MATLAB package hosted at https://github.com/Jfortin1/ComBatHarmonization/tree/master/Matlab.)

The harmonizer 358 can harmonize the identified imaging dataset and provide the harmonized dataset to a compute device (e.g., compute devices 101, 201, physician device 103). In the above example, after processing via combat, the final CH-CNR-NM voxels for each patient in the database can then be analyzed by a variety of different algorithms. In some implementations, as described, the harmonized dataset can be further evaluated and/or displayed in any suitable manner.

While the analysis device 305 is described to implement, via the processor 351, each of a data manager and the harmonizer, in other embodiments, an analysis device similar to the analysis device 305 can be configured with several instances of the above-mentioned units, components, and/or modules. For example, in some embodiments, the server may include several data managers, ML models, and/or harmonizers associated with one or more compute devices or groups of compute devices. Moreover, the terms data manager, ML model, and harmonizer are provided for illustrative purposes, e.g., to explain the processes implemented by the processor 351. Therefore, one or more of these modules can be combined into single modules or generally referred to as a processor configured to perform one or more processes or steps thereof. In addition, while the analysis device 305 is presented as a separate device from the compute device 201 but in communication in such compute device 201, it can be appreciated that the analysis device 305 and the compute device 201 (or other analysis devices and/or compute devices described herein) can be implemented on one or more devices that include suitable components (e.g., processors, memories, etc.) for performing the processes described with reference to each.

While the analysis device 305 is described herein to have a data manager, ML models, and harmonizer, in other embodiments an analysis device similar in structure and/or function to the analysis device 305 can be configured such that portions of the above described functions and/or modules can be carried out in and/or executed by compute devices that are included in the system (e.g., compute device 201) for example, via client side applications installed in the compute devices (e.g., within the data handler 214 of FIG. 2). Similarly stated, in some instances, functions described as being performed on an analysis device (e.g., analysis device 305) can be performed on a compute device 201 and vice versa.

In use, a compute device (e.g., compute device 201 or any of the other compute devices described herein) in a data harmonization system as described herein can receive imaging data associated with a region (e.g., tissue or organ) of interest of a patient obtained using an identified imaging equipment. The imaging data can be a biomarker specific MRI dataset (e.g., NM-MRI dataset). In some embodiments, the imaging data can be accompanied or can include supplemental data (e.g., meta data) indicating the clinical or biographical data associated with the patient, and/or data related to the scanning equipment associated with acquisition of the imaging dataset. Alternatively, the compute device can receive a the image data and the compute device can be configured to provide an interface to add supplemental information associated with the imaging data. The compute device can then send the information associated with the imaging data and/or send the imaging data to an analysis device in the data harmonization system. In some instances, the compute device can also send information indicating the one or more sources of variability that may be on interest and/or the one or more sources of variability that are undesired. In some instances, the compute device can be configured to register (also referred to herein as on-boarding) a scanning equipment (e.g., a new MRI scanner that is not registered in the data harmonization system). The registration data can include any suitable data associated with the registered scanning equipment (e.g., make, model, manufacture, time, location, station, institution of use, etc.), all pertinent data associated with the subject (e.g., biographic, demographic, and other health related information related to the patient, study, etc.) and coefficients determined by the system to reduce variability sourced from or associated with the equipment, patient, etc.

Figure 6:
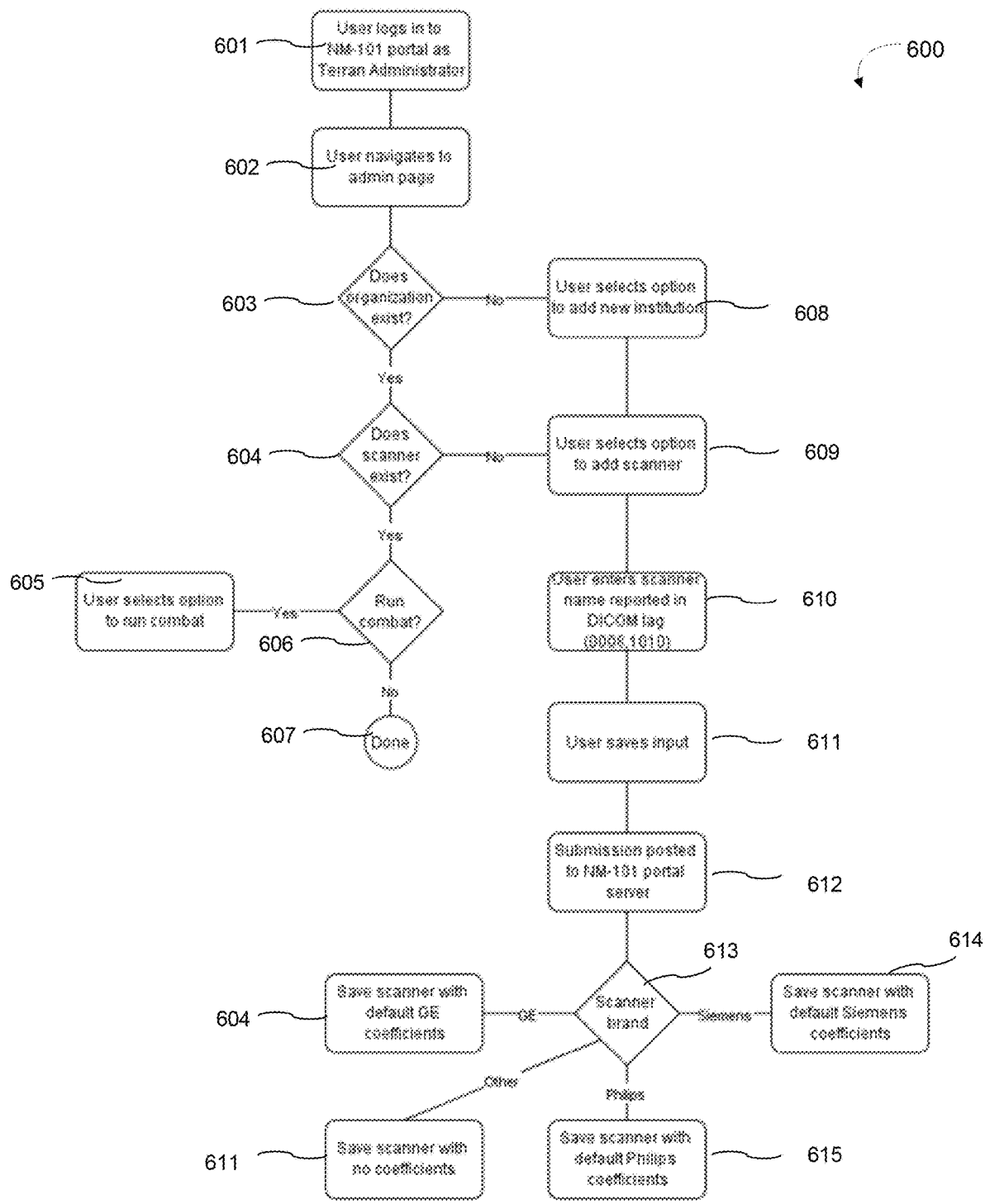
FIG. 6 is a flowchart describing a method of initiating preprocessing of information to obtain a harmonization of imaging data, using a data harmonization system, according to an embodiment.
Figure 7:
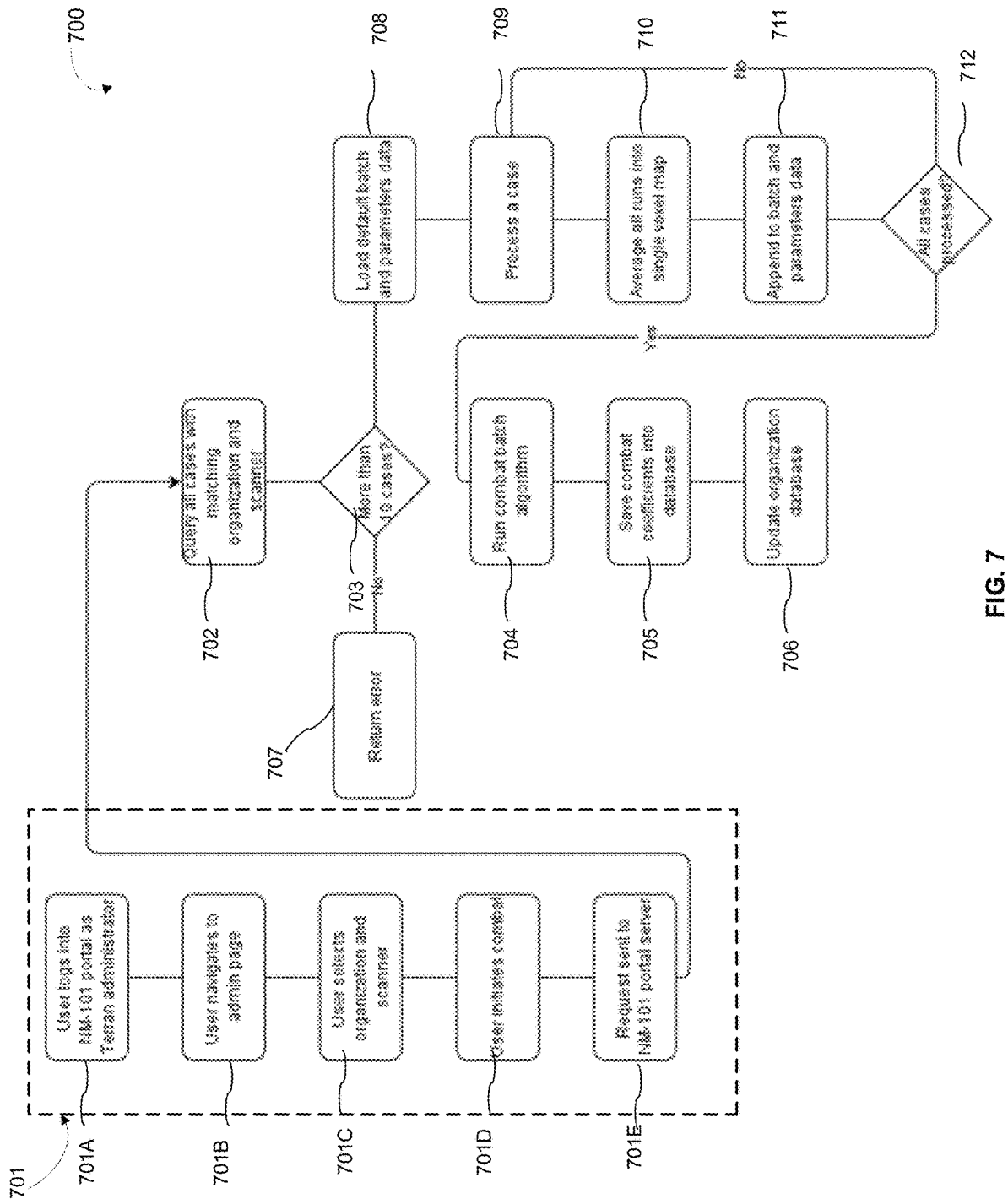
FIG. 7 is a flowchart describing a method of preprocessing information for harmonization of imaging data, using a data harmonization system, according to an embodiment.
Figure 8:
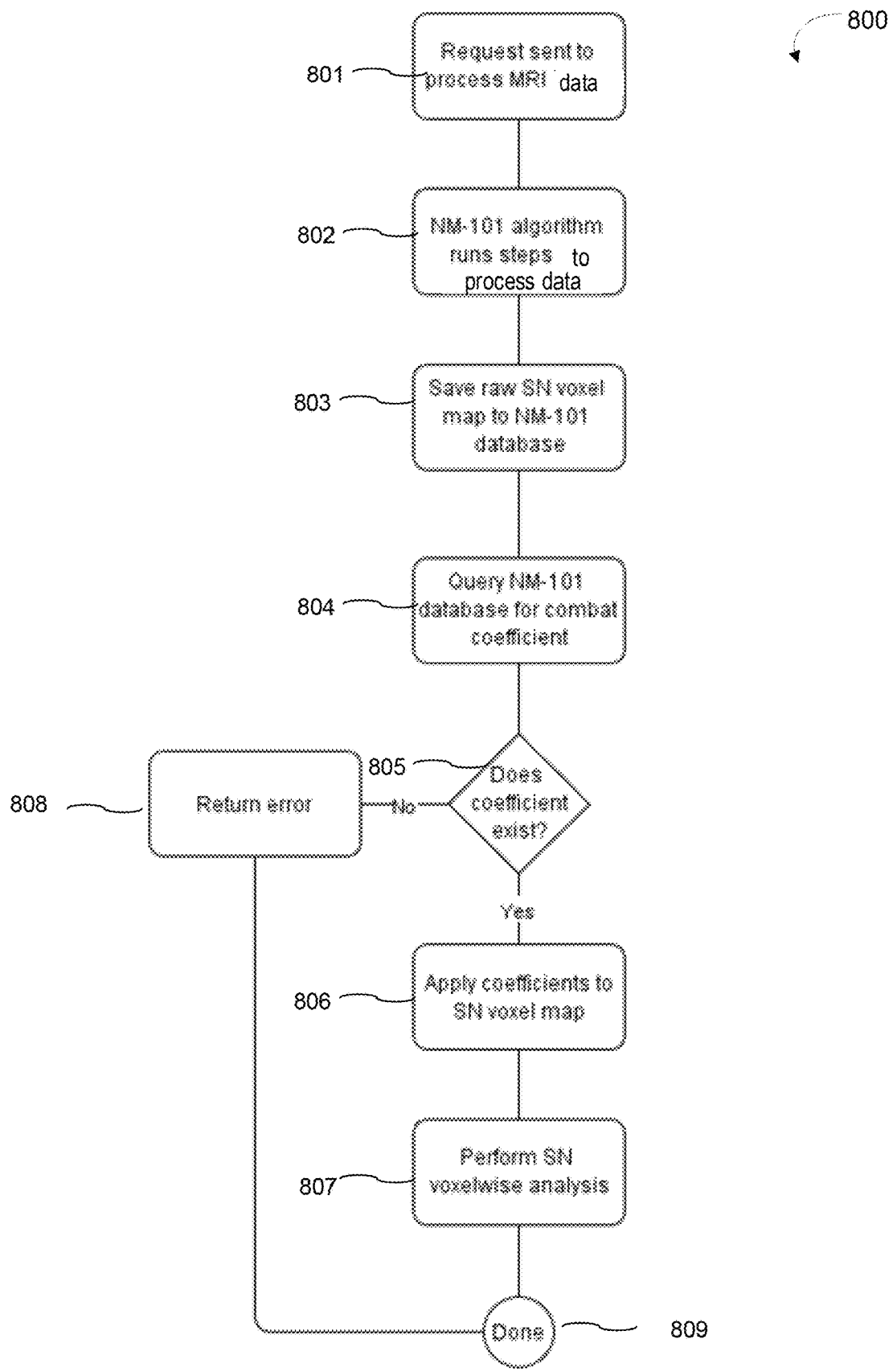
FIG. 8 is a flowchart describing a method of harmonization of imaging data, using a data harmonization system, according to an embodiment.

FIG. 6 shows a flowchart describing an example process of registering or on-boarding a new scanner, according to some embodiments. In some instances, the compute device can also indicate a reference dataset that is to be used to generate coefficients that when applied can harmonize an identified imaging dataset. The analysis device can receive the imaging data and the supplemental data and generate a set of coefficients by implementing an algorithm (e.g., ComBat algorithm). FIG. 7 shows a flowchart illustrating an example process of generating coefficients by an analysis device, according to some embodiments. In some implementations, the compute device can check for predetermined coefficients that may be applicable for harmonizing an identified imaging dataset. The compute device can identify and indicate a set of predetermined coefficients to be used to harmonize the identified imaging data set. For example, the compute device can indicate an identified scanning equipment that was used to generate an imaging dataset. The identified equipment can be a registered scanning equipment associated with the data harmonization system, the registration data being stored in a storage associated with the system. The registration data can include the registered scanning equipment and coefficients determined by the system to reduce variability sourced from or associated with the equipment. The analysis device can recognize the imaging equipment as pre-registered in the system, and determine the identity of the imaging equipment (e.g., manufacture, model, make, part number, etc.). The analysis device can determine and retrieve, from a storage associated with the system, the predetermined coefficients associated with the imaging equipment. The analysis device can then apply the coefficients to the identified imaging dataset to compute a harmonized imaging dataset having a reduced variability associated with the undesired sources of variability. FIG. 8 shows a flowchart illustrating an example process of applying coefficients to an imaging dataset to generate a harmonized dataset, according to an embodiment. The analysis device can then send the harmonized imaging dataset to the compute device. The compute device can suitably evaluate, display, and/or use the harmonized imaging data set (e.g., via an interface) as needed.

In some embodiments, data harmonization systems described herein (or components of such systems, such as any of the compute devices described herein) can be configured to work with any imaging, including any suitable biomarker specific MRI data.

A useful implementation of a method of harmonization of imaging data involves maintaining biologically meaningful variability (e.g., variability or differences associated with diagnostic status). When tailored to a specific biomarker, predetermined characteristics of the biomarker can be taken advantage of to adapt the harmonization process to best suit that biomarker specific imaging data. For example, neuromelanin (NM) is known to accumulate in dopaminergic midbrain neurons over the lifespan of a subject, NM-MRI signal can thus increase with age, providing biological variability that can be used to test a NM-MRI harmonization approach in healthy subjects. A possible added benefit of harmonization is the ability to improve both the reproducibility and statistical power of downstream analyses due to the removal of unwanted, nonbiological variability. This can be particularly beneficial for biomarker development where greater reproducibility and statistical power can lead to more generalizable biomarkers.

Figure 4:
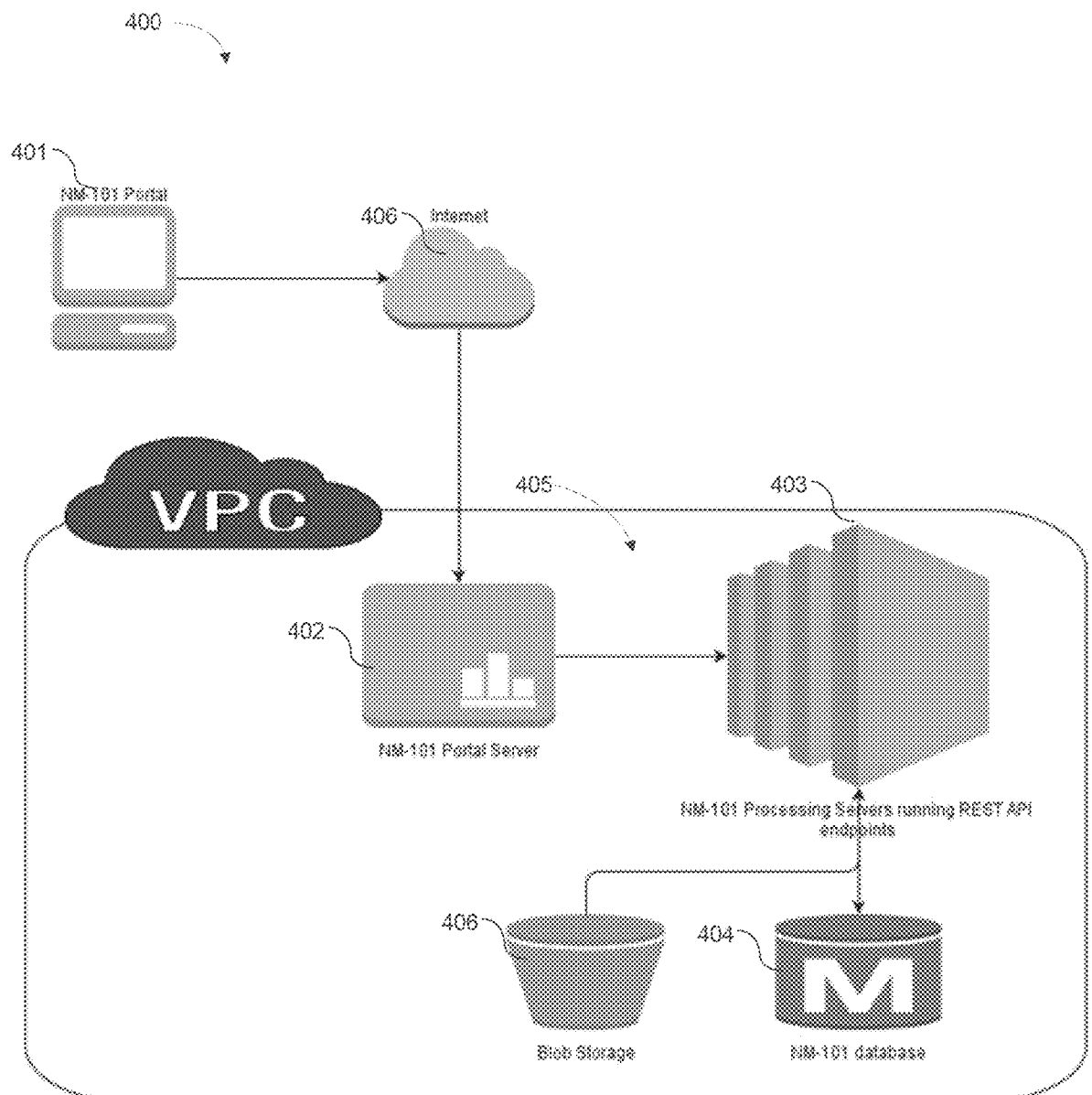
FIG. 4 is a schematic representing an example implementation of a data harmonization system, according to an embodiment.

FIG. 4 illustrates a flowchart describing an example implementation of harmonizing imaging data using a data harmonization system 400, according to an embodiment. The data harmonization system 400 can be substantially similar in structure and/or function to the data harmonization systems described herein (e.g., system 100). The data harmonization system 400 is implemented using a cloud—based architecture with one or more portions implemented using cloud-based computational systems in a cloud-based computational framework. The system 400 includes a compute device 401 that implements a portal NM-101 (e.g., a web-portal) configured to serve as an interface to communicate with the one or more cloud-based portions of the system 400 (e.g., the analysis device servers, database, storage, etc.). The compute device 401 of the system 400 communicates with the server systems collectively termed VPC via a communication network 406, which can be substantially similar to the communication network 106 described herein. The compute device 401 can be substantially similar in structure and/or function to the compute devices 101, 201 and/or analysis devices 105, 305 described above.

The cloud-based potion VPC of the system 400 includes an analysis device 405 that includes a portal server 402 and a processing server 403. The portal server 402 is configured to communicate with the compute device 401 via the NM-101 portal that serves as an interface for communication. The portal server 403 can receive instructions commands, data indications, etc. sent via the interface from the compute device 401 the instructions indicating the imaging datasets that are to be harmonized. The portal server 403 can receive metadata indicating the sources of variability that are undesired and to be reduced. For example,the portal server 402 can receive indication of the scanning equipment using to generate an imaging data set. In some implementations, the portal server can recognize the scanning equipment as not yet registered in the system 400. The portal server 402 can send instructions to the processing server to then generate a set of coefficients (e.g., by running a ComBat algorithm) that can be configured to reduce variability sourced from the scanning equipment and/or image acquisition parameters when applied on an imaging data set obtained using that scanning equipment. The processing server 403 can generate the coefficients using any suitable process.

In an example implementation, the processing server 403 can take up to a minute to complete to generate the coefficients. Once generated, the processing server 403 can send the coefficients and any other associated data to the NM-101 database 404 that can store the coefficients and the associated data for future use, and mark the scanning equipment as registered I the system 400. When the system 400 encounters new imaging data obtained from new scanning equipment, the system 400 can be configured to automatically or semi-automatically (i.e., with user provided inputs) generate new coefficients and store the coefficients while registering the scanning equipment (or any other suitable source of variability that may be desired to be reduced).

In the example implementation in FIG. 4, initiating the registration process at the portal server 402 via the NM-101 portal can trigger a REST API implemented by the system 400 to initiate the Combat algorithm. The ComBat algorithm can perform as follows:

1. Initiate a batch container with the 51 reference voxel maps used to generate the default ComBat coefficients.
2. Initiate a parameters container with the 51 reference age and genders used to generate the default combat coefficients. Note the reference age and genders align with the reference voxel maps. A container can be any suitable executable computational component. For example, in some instances, a container can be a discreet computational environment. The environment can be set up within an operating system in which one or more applications can be executed. In some implementations, a container can include an entity (e.g., a CSV file ".csv", or MAT file ".mat") holding a dataset including information associated with age and gender of the 51 references).
3. Query the NM-101 database for all cases that match the criteria {"scanner"=% TARGET_SCANNER %, "organization"=% TARGET ORGANIZATION %}. For each case, multiple SN voxel maps can be computed and stored for simultaneous runs.
4. For each case . . .
    a. Ignoring any voxel maps that have a NAN value in any of the voxels, compute an average SN voxel map and append it to the batch container.
    b. Append the age and gender to the parameters container.

Run the combat algorithm to generate new coefficients for the new scanner. Credit to https://github.com/Jfortin1/ComBatHarmonization for NeuroCombat algorithm in Python and Matlab.

Save coefficients to NM-101 database and link coefficients to target scanner.

Once the coefficients are generated and stored, the analysis device 405 (i.e. the portal server 402 or the processing server 403) can apply the coefficients to the imaging data to generate the harmonized data.

In some implementations, the compute device 401 or the portal server 402 can recognize the indicated scanning equipment as a registered scanner for which the system 400 has pre-generated coefficients. The portal server 402 can then retrieve the coefficients and send signals to the processing server 403, also implemented in the cloud-based framework VPC, to apply the coefficients.

Figure 5:
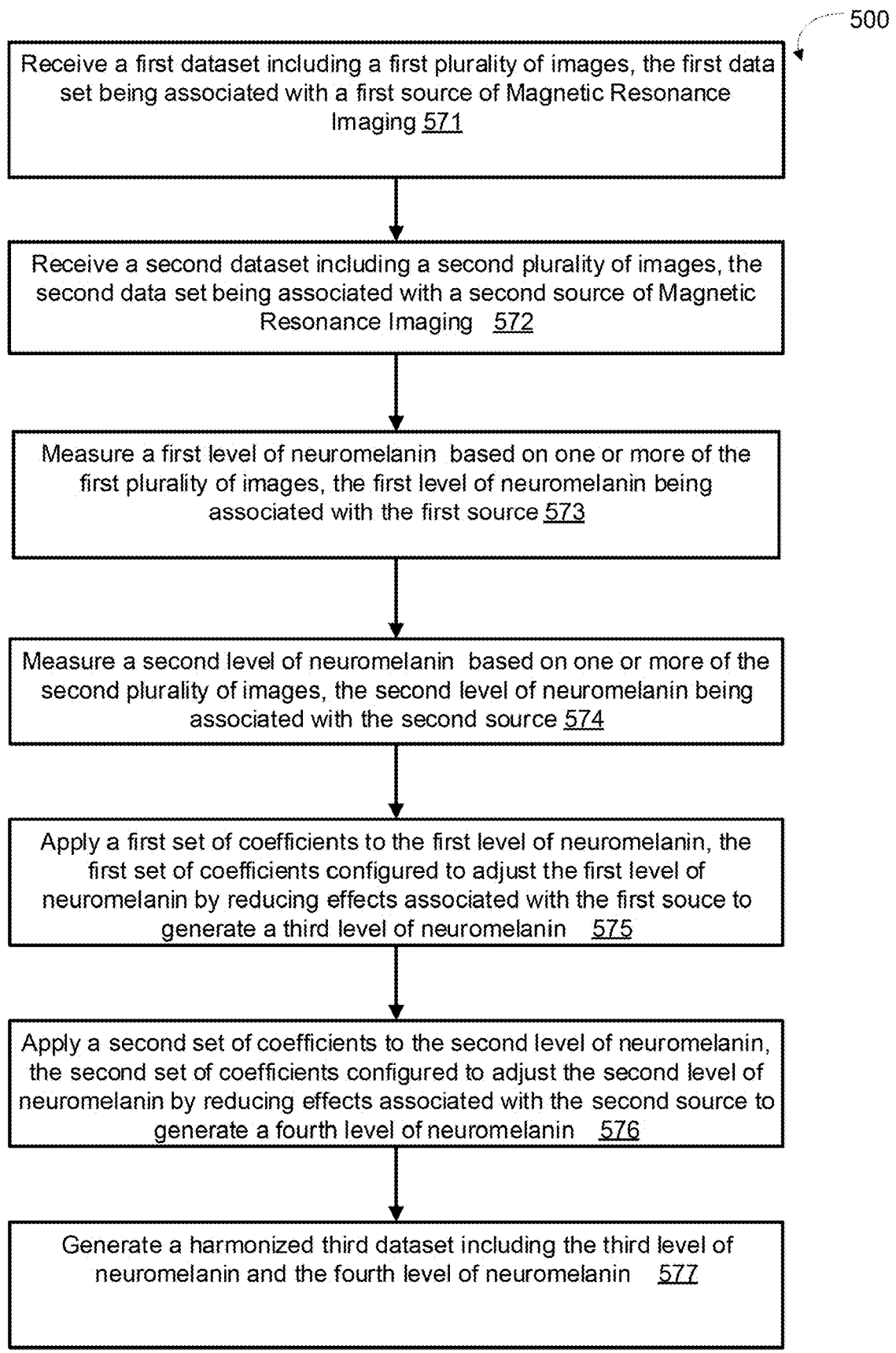
FIG. 5 is a flowchart describing a method of harmonizing scan data associated with two sources, using a data harmonization system, according to an embodiment.

As an example, before processing the SN voxelwise analysis, the combat coefficients can be applied to SN voxel map based on the recognized scanner that was used to capture the images. In some example implementations, the system 400 can use the InstitutionName DICOM tag (0008, 1010) and StationName DICOM tag (0008,0080) in the MRI images to identify the scanning institution and/or scanning equipment that is associated with an imaging data set. The system 400 can query the combat coefficient to be used for the identified institution and/or scanning equipment from the NM-101 database. The correct coefficients can be retrieved and applied to the SN voxel FIG. 5 illustrates a flowchart describing a method of generating a harmonized dataset using a data harmonization system, according to an embodiment. The method 500 can be implemented by a compute device that is similar in structure and/or function to the compute devices 101, 201, 401 and/or analysis devices 105, 305, 405 described above.

The method 500 includes, at 571, receiving a first dataset including a first plurality of images, the first data set being associated with a first source of Magnetic Resonance Imaging (MRI). The first dataset can be a biomarker specific MRI data set, for example an NM-MRI dataset associated with a first patient and acquired using a first MRI scanner.

At 572, the method includes receiving a second dataset including a second plurality of images, the second data set being associated with a second source of Magnetic Resonance Imaging. The second dataset can be a biomarker specific MRI data set, for example an NM-MRI dataset, associated with a second patient and/or acquired using a second MRI scanner.

At 573, the method 500 includes measuring a first level of neuromelanin based on one or more of the first plurality of images, the first level of neuromelanin being associated with the first source. As an example, the first level of neuromelanin can include CNR values associated with the first plurality of images.

At 574, the method 500 includes measuring a second level of neuromelanin based on one or more of the second plurality of images, the second level of neuromelanin being associated with the second source. The second level of neuromelanin can include CNR values associated with the second plurality of images.

At 575, the method 500 includes applying a first set of coefficients to the first level of neuromelanin, the first set of coefficients configured to adjust the first level of neuromelanin by reducing effects associated with the first source to generate a third level of neuromelanin. The first set of coefficients can be generated using a data harmonization system as described herein (e.g., by implementing a ComBat algorithm as described above). The third level of neuromelanin can be ComBat Harmonized (CH) CNR values associated with the first plurality of images, generated as described herein.

At 576, the method 500 includes applying a second set of coefficients to the second level of neuromelanin, the first second of coefficients configured to adjust the second level of neuromelanin by reducing effects associated with the first source to generate a fourth level of neuromelanin. The second set of coefficients can be generated using a data harmonization system as described herein (e.g., by implementing a ComBat algorithm as described above). The fourth level of neuromelanin can be ComBat Harmonized (CH) CNR values associated with the second plurality of images, generated as described herein.

At 577, the method 500 includes generating harmonized third dataset including the third level of neuromelanin and the fourth level of neuromelanin.

FIG. 6 is a flowchart illustrating an example process 600 that can be implemented by a data harmonization system, to on-board an unregistered scanner, according to an embodiment. The process in FIG. 6 can be implemented by any suitable device (e.g., compute device, analysis device, etc.) in a data harmonization system described herein. A user, for example, an administrator, can operate an interface (e.g., implemented by an interface manager 215) and navigate through the interface to check if information associated with as organization and/or scanner associated with an identified imaging data is available (exists). If so, the administrator can select options and enter information that link organization and scanner identity to the imaging data, and save the information on a database associated with the data harmonization system. If the scanner and/or organization already exists as a registered entry in the system, the imaging data can be linked to the preexisting entries such that predetermined coefficients associated with the entry can be used for harmonizing the imaging data. Based on the selection of scanner/organization the user may be prompted to initiate running the algorithm to generate coefficients and/or apply coefficients to harmonize the identified imaging data.

The process 600 includes, at 601, a user logging in to a portal (e.g., NM-101 portal) as an administrator. At 602, the process includes the user navigating to a control tool, for example, a page offered to users with administrative privileges, referred to as "admin page". At 603, the process includes a decision point evaluating whether an organization associated with a scanner used to acquire an identified imaging dataset is already registered or present in the data harmonization system. If the choice in response to the decision at 603 is "Yes" the process 600 includes, at 604 a decision point evaluating if the scanner used to acquire an identified imaging dataset is already registered or present in the data harmonization system. If the choice at 604 is "Yes", the process 600 includes, at 606 a decision point querying the user whether to execute a data harmonization algorithm (e.g., ComBat algorithm) on the identified imaging dataset based on the registered information associated with the organization and the scanner. A response indicating Yes to the query at 606 leads to 605 where the process includes the user selecting the option to run the data harmonization algorithm. Alternatively, if the choice in response to the decision at 603 is "No" the process includes, at 608, the user or administrator selecting a control tool, for example, in the form of an option, to add a new institution as an organization into the system's database. Similarly, if the choice in response to the decision at 604 is "No" the process includes, at 609 (also reachable from 608), the user or administrator selecting a control tool, for example, in the form of an option, to add a new scanner into the system's database. At 610 the user can add the details of the scanner (e.g., from name of the scanner reported in DICOM tag if the imaging data is in DICOM format). At 611, the process includes the user saving the input regarding the scanner and/or the organization. At 612, the process includes submitting the input into the portal server to be saved in a database associated with the system. At 613, the process includes a decision point to indicate the brand of the scanner added. As an example, if the scanner is from manufacturer Siemens, the process includes at 614, saving the scanner with predetermined or default coefficients associated with scanners manufactured by Siemens. At 615, the process includes determining the scanner is from Phillips and saving the scanner with predetermined or default coefficients associated with scanners manufactured by Phillips. At 604, the process includes determining the scanner is from GE and saving the scanner with predetermined or default coefficients associated with scanners manufactured by GE. At 611, the process includes determining the scanner is not from one of the identified manufacturers and saving the scanner with no default coefficients.

FIG. 7 is a flowchart illustrating an example process 700 that can be implemented by a data harmonization system, to initiate and implement generating and saving coefficients to harmonize a dataset, according to an embodiment. The process in FIG. 7 can be implemented by any suitable device(e.g., compute device, analysis device, etc.) in a data harmonization system described herein. The portion 701 of the process 700 within the dashed lined box can be implemented in a compute device (e.g., compute devices 101, 201, 401) in communication, via a portal, with an analysis device (e.g., 105, 305, 405) described herein with reference to systems 100 and 400, in FIGS. 1, 2, 3, and 4. As shown, a user can select organization and scanner associated with an imaging dataset, and initiate the algorithm (e.g., ComBat algorithm) via a portal, to generate and/or apply coefficients to harmonize the imaging data. The request can be received via the portal and the system can search its databases for a preexisting and matching organization and scanner that is already registered in the system. If there are more than 10 matches, the system can load a default batch that can be used a reference for the identified organization or scanner. The default batch can be used to generate a voxel map which can be used to run the algorithm. Once generated the coefficients can be stored in a database (i.e., update information associated with the identified organization and/or scanner in the database). If there are not more than ten cases the system is shown to return an error. In some instances, the system can be configured to perform other operations such as adopt a predetermined reference map or the like.

The process 700 includes, at 701, a user initiating data harmonization by sending a request for an execution of a data harmonization algorithm (e.g., ComBat algorithm). The portion 701 includes at 701A a user logging into a portal (e.g., NM-101 portal) and at 701B, navigating to a control page. The process includes at 701C the user selecting an organization and a scanner associated with an identified imaging dataset that is to be harmonized, and at 701D initiating the execution of the data harmonization algorithm (e.g., ComBat algorithm). At 701E the process includes sending a request (e.g., from a compute device such as compute device 101, 201, and/or 401) where the portion 701 can be implemented. The process 700 further includes at 702, a query of all cases in a database associated with the system, the query configured to find matches between the organization indicated (in the request at 701E) as associated with the identified imaging data and the organizations saved in the system. The query at 702 also includes a search of all cases in a database associated with the system to find matches between the scanner indicated (in the request at 701E) as associated with the identified imaging data and the scanners saved in the system. The process 700 includes at 703, a decision point evaluating whether there are more than a specified or threshold number of cases found as hits in response to the query at 702. The threshold can be any desired number. In the example in FIG. 7, the evaluation at 703 is whether there are more than 10 cases found as matches. If the response is No,the process returns, at 707, an error. Alternatively, if the response to the evaluation at 703 is Yes (i.e., there are more than 10 cases found as matches in response to the query at 702) the process includes at 708, and for each of the identified cases, loading a default batch (e.g., default batch of imaging data for that case) and parameters data (e.g., default image acquisition parameters associated with the identified scanner and/or organization for that batch of imaging data) associated that case. At 709, the process includes processing that case (i.e., processing the default batch of imaging dataset based on the parameters data). The process incudes at 710, averaging all runs (imaging runs) each run including a set of voxels, into a single voxel map. At 711, the process includes appending to the batch of imaging data the single voxel map, and append to the parameters data, one or more parameters associated with the identified imaging data set. At 712, the process includes evaluating whether all cases are processed. If not, the steps 709-711 are implemented for each case as described herein. If the choice is yes in response to the evaluation at 712, the process includes at 704, running the data harmonization algorithm (ComBat algorithm) on the identified imaging data to generate coefficients associated with the scanner and organization associated with the identified imaging dataset. At 705, the process includes saving the coefficients and at 706, the process includes updating the information I the data base associated with the organization to include the information and coefficients generate at 705.

FIG. 8 is a flowchart illustrating an example process 800 that can be implemented by a data harmonization system, to apply coefficients to harmonize a dataset, according to an embodiment. The process 800 in FIG. 8 can be implemented by any suitable device(e.g., compute device, analysis device, etc.) in a data harmonization system described herein. As shown, the system can generate or retrieve coefficients (as described herein) and apply the coefficients to imaging data (e.g., SN voxel map derived from a plurality of images). The system can perform voxelwise analysis to generate a harmonized dataset.

The process 800 includes, at 801, sending a request to process an MRI data (e.g., MRI imaging data), which can be a biomarker-specific MRI imaging data such as NM-MRI. The imaging data can include, for example, voxel values associated with the SN or VTA area of the brain acquired from a subject. The request can be sent from a compute device (e.g., compute devices 101, 201, 401) in communication, via a portal, with an analysis device (e.g., 105, 305, 405) described herein with reference to systems 100 and 400, in FIGS. 1, 2, 3, and 4, and with reference to process 600 in FIG. 6. At 802, the process 800 includes running an algorithm (e.g., NM-101 algorithm) to process the data. The processing of the data at 802 can include processes 600 and/or 700 described above. As an example, the processing can result in a voxel map associated with the imaging data. At 803, the process 800 includes saving the raw voxel map to the database associated with the data harmonization system. For example, the voxel map can be a SN voxelmap associated with the SN area of the brain and/or including indications of the biomarker of interest (e.g., NM) as described herein. At 804, the process includes querying the database for coefficients associated with the scanner and organization associated with the identified imaging data. At 805, the process includes evaluating whether suitable coefficients exist in the database of the system. If the response to the evaluation at 805 is yes (e.g., positive identification and retrieval of suitable coefficients), the process includes at 806, applying the coefficients retrieved from the database to the SN voxelmap of the identified imaging data. At 807 the process includes performing a SN voxelwise analysis to generate a harmonized dataset, thereby completing the harmonization of the identified imaging data set at 809. If the response to the evaluation at 805 is No, the process includes at 808 a return of error indicating that the identified imaging data set is unable to be harmonized as requested.

EXAMPLE STUDIES

A. Cross-Scanner Harmonization of Neuromelanin-Sensitive MRI for Multisite Studies An example implementation of systems and methods described herein were used for harmonization of NM-MRI data from 3 major MRI vendors (GE, Siemens, and Philips) with acquisition parameters that were not optimized across sites. The example studies show that the method successfully harmonized the NM-MRI data while maintaining biologically meaningful variability (increased NM-MRI signal with age) and that it improved both the reproducibility and statistical power of the expected positive relationship between the NM-MRI signal and age.

Datasets: NM-MRI and anatomical T1-weighted MRI data were collected on 128 healthy subjects from studies at Columbia University, the University of Amsterdam, and Stony Brook University. At Columbia University, 51 subjects were collected on a 3T GE MR750 (mean [SD] age: 34.5 [14.6] years; 22 female and 29 male) and 29 subjects on a 3T GE Signa Premier (mean [SD] age: 29.0 [7.4] years; 15 female and 14 male); at the University of Amsterdam, 12 subjects were collected on a 3T Philips Ingenia (mean [SD] age: 23.9 [4.1] years; 4 female and 8 male); and 12 subjects on a 3T Philips Ingenia Elition (hereafter referred to as Philips Elition; mean [SD] age: 24.3 [2.1] years; 5 female and 7 male); and at Stony Brook University, 24 subjects were collected on a 3T Siemens Prisma (mean [SD] age: 27.8 [8.9] years; 12 female and 12 male). No subjects had a history of neurological or psychiatric disorder as determined by subject report. Due to hardware and/or software differences, the NM-MRI sequence parameters differed across MRI scanners; a detailed description of sequence parameters is given in Table 1.

TABLE 1

NM-MRI Acquisition Parameters.

| Parameter | CU | | UA | | SBU |
| --- | --- | --- | --- | --- | --- |
| | GE MR750 | GE Signa Premier | Philips Ingenia | Philips | Siemens Prisma |
| RO FOV (mm) | 220 | 220 | 199 | 199 | 220 |
| PE FOV (mm) | 165 | 165 | 162 | 162 | 165 |
| SS FOV (mm) | 30 | 30 | 22 | 22 | 30 |
| RO Resolution | 0.43 | 0.43 | 0.39 | 0.39 | 0.43 |
| PE resolution (mm) | 0.43 | 0.43 | 0.39 | 0.39 | 0.43 |
| SS resolution (mm) | 3 | 1.5 | 2.5 | 2.5 | 3 |
| RO matrix | 512 | 512 | 512 | 512 | 512 |
| PE matrix | 320 | 320 | 416 | 416 | 320 |
| Number of slices | 10 | 20 | 8 | 8 | 10 |
| Slice gap (mm) | 0 | 0 | 0.25 | 0.25 | 0/0 |
| TE (ms) | 3.9 | 4.8 | 3.9 | 3.9 | 3.9 |
| TR (ms) | 250 | 500 | 260 | 260 | 273 |
| FA (°) | 40 | 40 | 40 | 40 | 40 |
| NEX | 8 | 5 | 2 | 2 | 10 |
| Averaging mode | Online | Online | Online | Online | Offline |
| BW (Hz/Px) | 122 | 122 | 75 | 75 | 315 |
| MT offset (Hz) | 1200 | 1200 | 1200 | 1200 | 1200 |
| MT duration (ms) | 10 | 10 | 15.6 | 15.6 | 10 |

Labels: CU, Columbia University; UA, University of Amsterdam; SBU, Stony Brook University; RO, read-out direction; FOV, field-of-view; PE, phase-encoding direction; SS, slice-selection direction; TE, echo time; TR, repetition time; FA, flip angle; NEX, number of averages; BE, bandwidth; MT, magnetization transfer pulse.

Data processing: The data processing methods described herein can be implemented using a compute device, examples of which are described above with reference to FIGS. 1-3. NM-MRI data were preprocessed using a procedure pipeline combining Statistical Parametric Mapping (SPM) and Advanced Normalization Tools (ANTs) previously shown to achieve excellent test-retest reliability. An example procedure included the following steps: (1) if averages were acquired separately (e.g. offline), realignment to correct for motion using 'SPM-Realign' and averaging of the realigned images using 'SPM-ImCalc'; (2) brain extraction of the T1w image using 'antsBrainExtraction.sh'; (3) spatial normalization of the brain-extracted T1w image to MNI152NLin2009cAsym space using 'antsRegistrationSyN.sh' (rigid+affine+deformable syn); (4) coregistration of the NM-MRI image to the T1w image using 'antsRegistrationSyN.sh' (rigid); (5) spatial normalization of the NM-MRI images to MNI space, defined according to the standard MNI template for MRI scans, by a single-step transformation combining the transformations estimated in steps (3) and (4) using 'antsApplyTransforms'; (6) spatial smoothing of the spatially-normalized NM-MRI image with a 1 mm full-width-at-half-maximum Gaussian kernel using 'SPM-Smooth'.

The preprocessed NM-MRI images in MNI template space were then used to estimate NM-MRI contrast ratio (CNR) maps. NM-MRI CNR at each voxel was calculated as the percent signal difference in NM-MRI signal intensity at a given voxel ($I_V$) from the signal intensity in the crus cerebri ($I_{CC}$)—a region of white matter tracts known to have minimal NM content—as:

$CNR_V = \{[I_V - \text{mode}(I_{CC})]/\text{mode}(I_{CC})\} \times 100$, where mode ($I_{CC}$) was calculated for each participant from a kernel-smoothing-function fit to a histogram of all voxels in the CC mask.

CNR values of the 1,807 voxels in the substantia nigra-ventral tegmental area complex (SN-VTA) mask were then harmonized using the ComBat harmonization model to remove nonbiological variability (e.g., variability associated with variations in MRI scanners) while maintaining biological variability associated with age and gender. This procedure can be comparable with harmonization of outcome measures (e.g., SN-VTA CNR or regional brain volumes) instead of the raw MRI signal. The computation model can be written as:

$$y_{ijv} = \alpha_v + X_{ij}^T \beta_v + \gamma_{iv} + \delta_{iv} \varepsilon_{ijv}$$

where $y_{ijv}$ is the CNR value of MRI scanner i, (i ∈ {1, ..., 5}), subject j(j ∈ {1, ..., 128}), and SN-VTA voxel v (v ∈ {1, ..., 1807 }); $a_v$ is the average CNR value for SN-VTA voxel v; X is a design matrix for the covariates of interest (age and gender); $\beta_v$ is a vector of regression coefficients corresponding to X for SN-VTA voxel v; $\gamma_{iv}$ and $\beta_{iv}$ are the additive and multiplicative effects of MRI scanner i for SN-VTA voxel v, respectively; and $\varepsilon_{ijv}$ are the error terms that are assumed to follow a normal distribution with mean 0 and variance $\sigma_v^2$.

The ComBat-harmonized CNR values are defined as:

$$y_{ijv}^{ComBat} = \frac{y_{ijv} - \hat{\alpha_v} - X_{ij}\hat{\beta_v} - \gamma_{iv}^*}{\delta_{iv}^*} + \hat{\alpha_v} + X_{ij}$$

where $\gamma_{iv}^*$ and $\delta_{iv}^*$ are the empirical Bayes estimates of $\gamma_{iv}$ and $\delta_{iv}$ respectively. Harmonization of the SN-VTA CNR was performed using a publicly available MATLAB package hosted at https://github.com/Jfotin1/ComBatHarmonization/tree/master/Matlab.

Harmonization was also performed on the raw MRI signal (e.g., NM-MRI signal within the CC and the SN-VTA separately prior to calculating CNR) but failed to remove the nonbiological variability (data not shown).

Figures 9A, 9B:
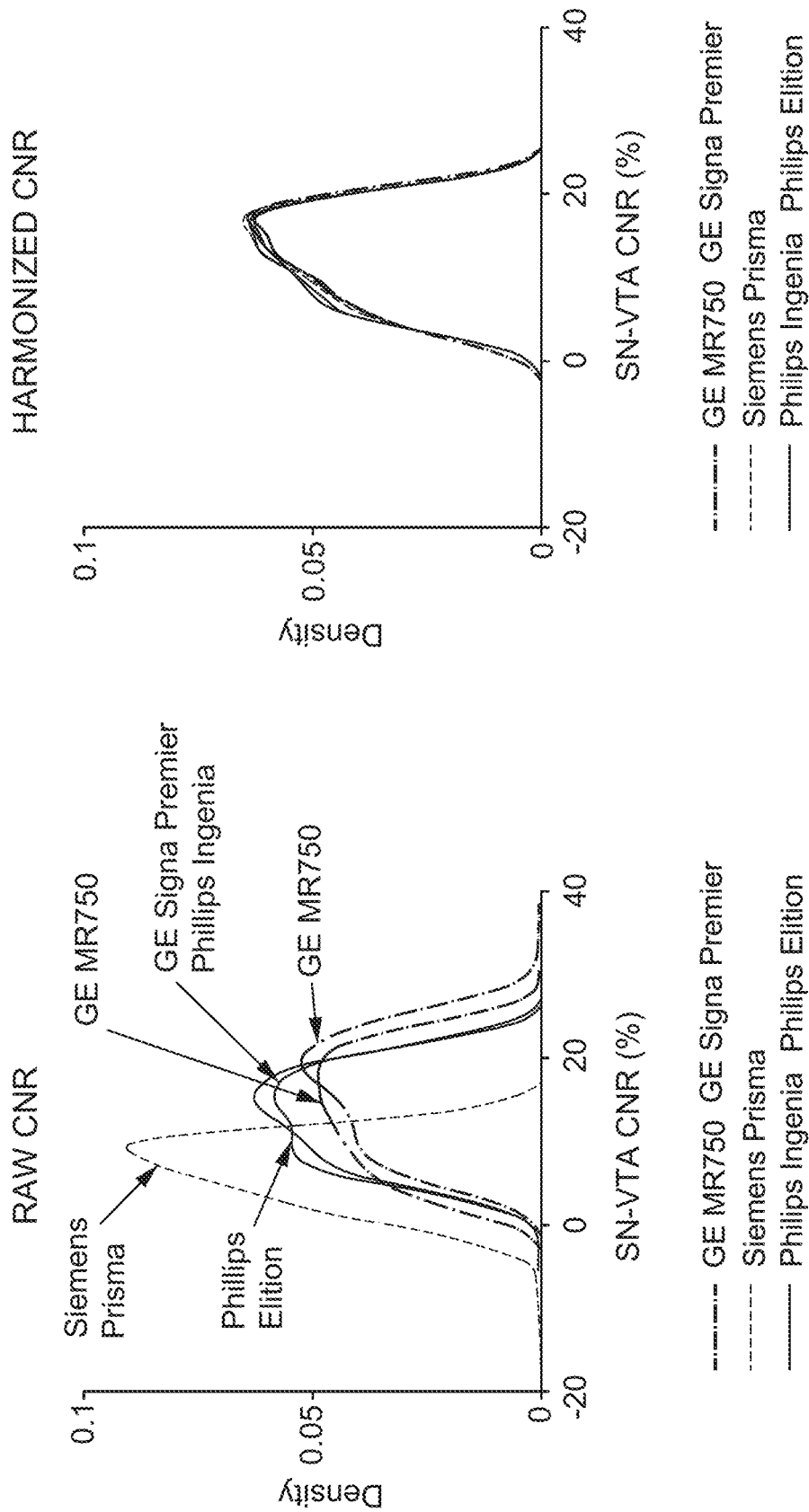
FIGS. 9A and 9B are graphical representations of example imaging data obtained from Neuromelanin-sensitive magnetic resonance imaging (NM-MRI) using multiple imaging sources, before and after harmonization using a data harmonization system, according to an embodiment, respectively.
Figure 10B:
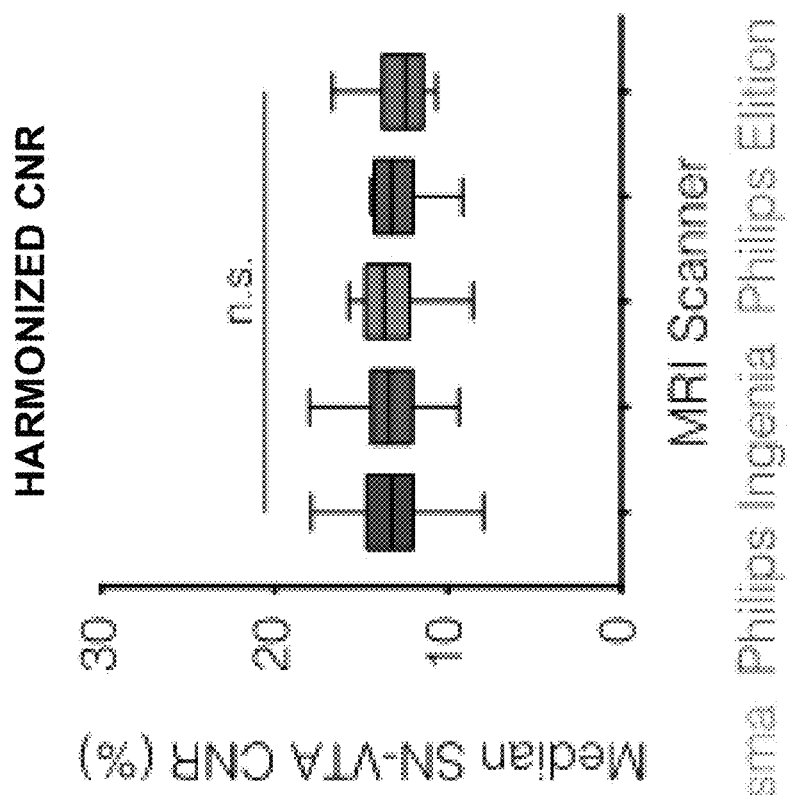
FIGS. 10A and 10B are graphical representations of example imaging data obtained from NM-MRI using multiple imaging sources, before and after harmonization using a data harmonization system, respectively, according to an embodiment.
Figure 10A:
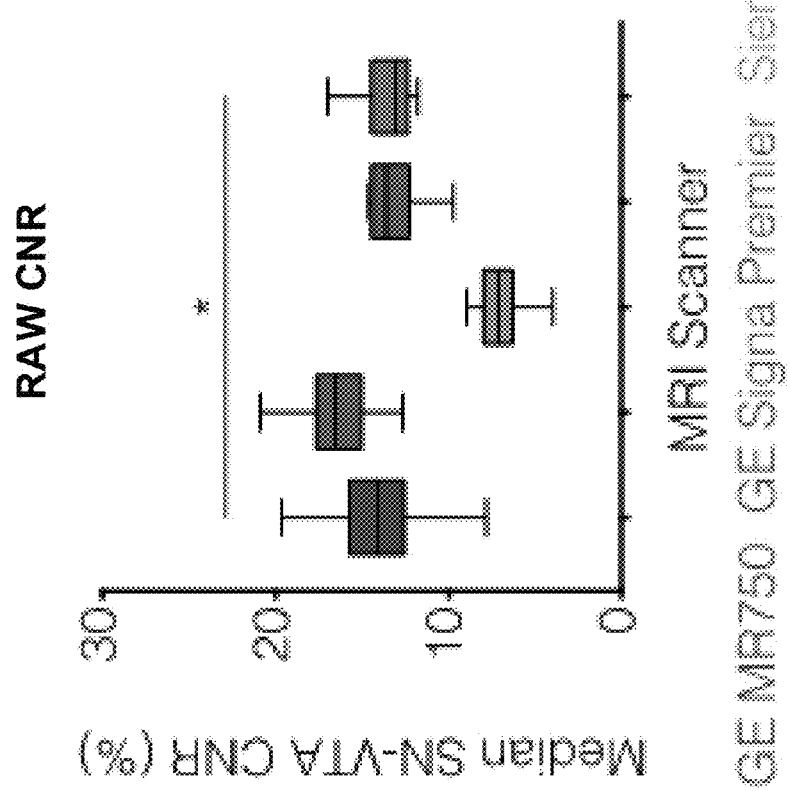

FIGS. 9A and 9B, and FIGS. 10A and 10B show results of harmonization of imaging data acquired using the variety of scanners. Specifically, the mean SN-VTA CNR distributions across subjects within each scanner were calculated and compared across scanners As shown in FIGS. 9A, distributions of SN-VTA CNR values obtained from imaging using the five different scanners of three different types shows that scanner effects are apparent (in the form of shifts and scaling differences in the distributions) in NM-MRI data. FIG. 10A shows the spread of the data in distributions shown in FIG. 9A, in the form of box plots. The asterisk (*) denotes $p<0.05$ for an ANOVA comparing the means of the median SN-VTA CNR distributions across MRI scanners. The variability in the data associated with variations in scanner, acquisition parameters, etc. can be seen by the spread of the means and the standard deviations indicated by the box plots in FIG. 10A, each box plot being associated with each scanner listed (GE MR750, GE Signa Premier, Siemens Prisma, Phillips Ingenia, and Phillips Elition, from left to right). FIG. 9B shows distributions of the SN-VTA CNR values obtained from imaging after harmonization of the datasets. As shown, the scanner effects, for example, the variability due to the differences between scanners and/or acquisitions parameters, etc., can be removed via harmonization of the data sets as indicated by the normalized appearance of the distributions following harmonization, with all distribution having comparable means, standard deviations, scaling, etc. FIG. 10B shows the spread of the harmonized data in distributions shown in FIG. 9B, in the form of box plots, each box plot being associated with each scanner listed (GE MR750, GE Signa Premier, Siemens Prisma, Phillips Ingenia, and Phillips Elition, from left to right). Notation "n.s." denotes that the data was not significant for an ANOVA comparing the means of the median SN-VTA CNR distributions across MRI scanners. In the raw CNR, the median across SN-VTA voxels differed significantly between scanners ($F4,123=72.45$, $p<10-30$, one-way ANOVA; FIG. 9A). In the harmonized CNR, the difference was no longer apparent ($F4,123=0.13$, $p=0.969$, one-way ANOVA; FIG. 9B), as indicated by the comparable means or means that are closer together in value for the data from the scanners.

Classification of MRI scanner: The evaluation described herein can be implemented using a compute device, examples of which are described above with reference to FIGS. 1-3. Following a previous application of ComBat to MRI data, the performance of the NM-MRI harmonization method was evaluated. The evaluation was performed by classifying MRI scanners (GE MR750, GE Signa Premier, Philips Ingenia, Philips Elition, and Siemens Prisma) using support vector machines (SVM) based on the pattern of SN-VTA CNR. Specifically, the input features for the SVM were the 1,807 voxelwise CNR values within the SN-VTA mask. Average classification accuracy was estimated using 5-fold cross-validation (1,000 repetitions) of a one-vs-one error correcting output code linear SVM (MATLAB, fitcecoc with hyperparameter C optimized in an inner 3-fold cross-validation loop)—previously shown to improve performance over other multiclass classifiers—for the raw and ComBat harmonized CNR separately. To account for imbalanced sample sizes across scanners, misclassification costs were set to be inversely proportional to class frequencies for each one-vs-one classifier. Statistical significance was determined using a permutation test in which MRI scanner labels were randomly shuffled 10,000 times.

Figure 11:
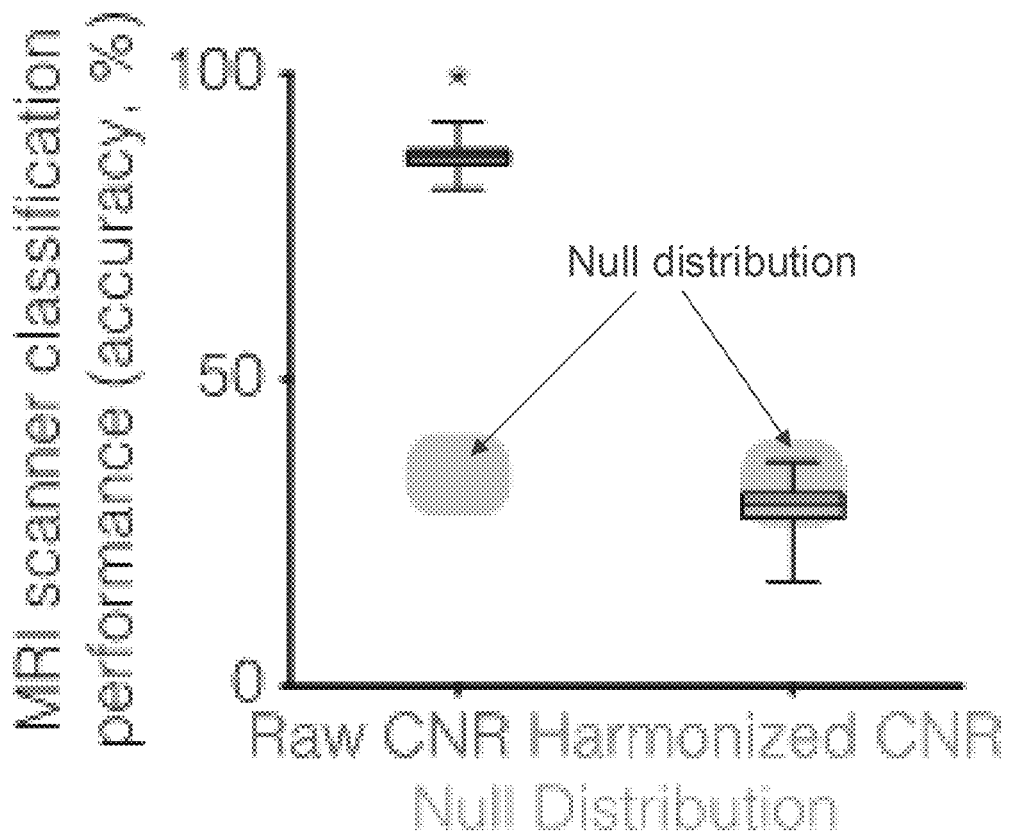
FIG. 11 is a graphical representation of classification of imaging source based on example imaging data obtained from NM-MRI using multiple imaging sources. The representation shows classification performance based on imaging data, before and after harmonization using a data harmonization system, according to an embodiment.

FIG. 11 shows results of classification before and after harmonization of data, using a data harmonization system according an embodiment. FIG. 11 shows boxplots with the mean performance for classification of MRI scanner using 5-fold cross-validated linear SVM across 1,000 random splits of the data. The null distributions indicate empirical chance-level performance ($2.5^{th}$-$97.5^{th}$ percentile shown) determined by randomly shuffling each subject's MRI scanner label 10,000 times. The asterisk (*) denotes $p<0.05$ for the permutation test comparing the mean classification accuracy over the 1,000 random splits to the null distribution. For all boxplots, the minimum, $25^{th}$ percentile, $50^{th}$ percentile (median), $75^{th}$ percentile, and maximum are shown. Results from SVM classification of MRI scanner confirmed the differences between scanners (shown as separation from the null distribution in the raw imaging data plotted on the left side in FIG. 11) and the ability to remove them via ComBat (shown as no separation from the null distribution in the Harmonized CNR data plotted on the right side in FIG. 11). Like with the univariate analysis on the summary statistics (see FIGS. 9A, 9B, 10A, and 10B), a multivoxel pattern analysis (MVPA) based on an SVM classifier using all voxelwise raw CNR in the SN-VTA mask showed high, above-chance accuracy for MRI scanner classification (mean±standard deviation test accuracy=86.5±1.8%, 5-fold cross-validation; $p=0.0001$, permutation test; FIG. 11). In the harmonized CNR, the accuracy of the SVM classifier was no longer above chance (test accuracy=29.5±3.0%; $p=0.8542$, permutation test; FIG. 11).

B. NM-MRI Harmonization Maintains Biologically Meaningful Variability

To evaluate whether harmonization of NM-MRI data preserved interindividual variability in a biologically meaningful variable, used SVR was used to predict age using all voxelwise SN-VTA CNR—because NM accumulates with age. The analyses described herein can be implemented using a compute device, examples of which are described above with reference to FIGS. 1-3.

Multivariate prediction of age: To determine the ability of the proposed NM-MRI harmonization method to maintain biologically meaningful variability, linear epsilon-insensitive support vector regressions (SVR) was used to predict age from the voxelwise pattern of SN-VTA CNR. Specifically, the input features for the SVR were the 1,807 voxelwise CNR values within the SN-VTA mask. Root-mean-square error (RMSE) and Pearson correlation coefficient (r) between the actual and predicted ages were estimated using 10-fold cross-validation (1,000 repetitions) linear SVR (MATLAB, fitrlinear with hyperparameter C optimized in an inner 5-fold cross-validation loop) for the raw and ComBat harmonized CNR separately. Statistical significance was determined using a permutation test in which age values were randomly shuffled 10,000 times for surrogate subjects. To determine the reproducibility of the age-prediction results, 1,000 random subsets of subjects of varying sample sizes (32, 64, and 96) were selected and the Pearson correlation coefficient (r) between the SVR β-coefficients for each subset with the same sample size was calculated separately for the raw and ComBat harmonized CNR. Due to significant site effects observed in the raw CNR, site was regressed out for each feature prior to input in the SVR.

Standard Univariate Voxelwise Analysis of Age Effects

To determine the statistical power of the age effects (significant positive relationship with age), a standard voxelwise analysis wase performed via a robust linear regression analysis (MATLAB, fit/m with 'RobustOpts', 'on') that predicted CNR at every voxel v within the SN-VTA as follows:

$$CNR_v = \beta_0 + \beta_1 \cdot age + \Sigma_{i=2}^{n+2} \beta_i \cdot \text{nuisance covariate} + \epsilon$$

where n=5 for the raw CNR (gender and 4 dummy variables for the 5 MRI scanners as nuisance covariates) and n=1 for the harmonized CNR (gender as a nuisance covariate). To correct for multiple comparisons, we defined the spatial extent of an effect as the number of voxels, k, exhibiting a significant correlation with age (voxel-level height threshold for t-test of regression coefficient $\beta_1$ of p<0.05, one-sided). Statistical significance was determined using a permutation test in which age values were randomly shuffled 10,000 times as above. The variability of the effect size (k) was determined using a leave-one-out procedure in which average CNR for a given subject was extracted from the voxels with a significant effect in the remaining subjects.

Figure 12B:
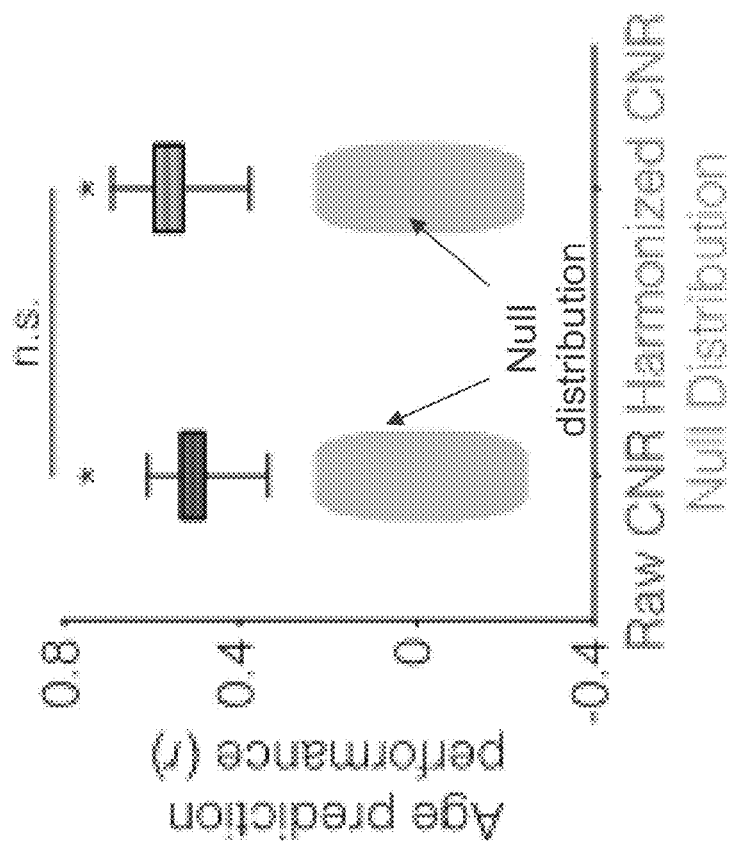
FIGS. 12A and 12B are graphical representations of biologically meaningful variability associated with example imaging data obtained from NM-MRI using multiple imaging sources, before and after harmonization using a data harmonization system, respectively, according to an embodiment.
Figure 12A:
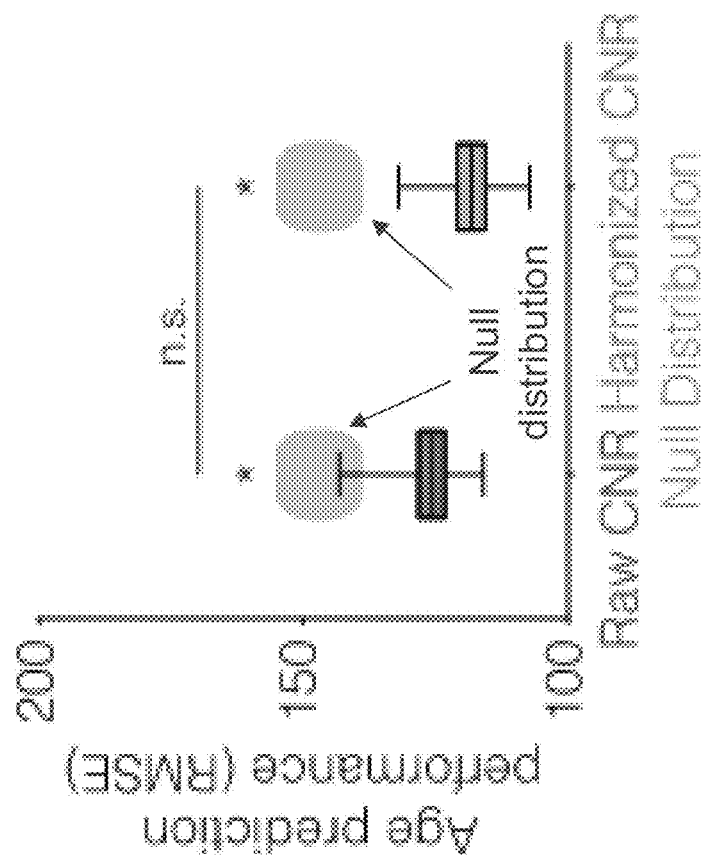

The results indicated that ComBat harmonization of NM-MRI SN-VTA CNR maintains biologically meaningful variability associated with age. SVR based on the raw CNR could predict age significantly above chance because NM accumulates with age and this variability was maintained through the harmonization procedure. The results shown in FIGS. 12A and 12B show boxplots with the mean performance for age prediction using 10-fold cross-validated linear SVR across 1,000 random splits of the data for two performance metrics: root-mean square error (RMSE; FIG. 12A) and Pearson correlation coefficient (r; FIG. 12B). The null distributions indicate empirical chance-level performance ($2.5^{th}$-$97.5^{th}$ percentile shown) determined by randomly shuffling each subject's age 10,000 times. Asterisks (*) denote p<0.05 for the permutation test comparing the mean age prediction performance over the 1,000 random splits to the null distribution. n.s.: not significant for the permutation test comparing the mean age prediction performance between the raw and harmonized CNR. For all boxplots, the minimum, $25^{th}$ percentile, $50^{th}$ percentile (median), $75^{th}$ percentile, and maximum are shown. Note that site effects in the raw CNR were regressed out for each feature prior to input in the SVR. The results indicated that The SVR based on the raw CNR could predict age significantly above chance (mean±standard deviation RMSE=125.91±3.83 months, 10-fold validation; p=0.0002, FIG. 12A, and permutation test; r=0.51±0.04; p=0.0002, permutation test FIG. 12B). Performance was also significantly above chance based on the harmonized CNR (RMSE=118.35±3.99 months, p=0.0002, permutation test; FIG. 12A, and r=0.56±0.05; p=0.0002, permutation test; FIG. 12B), suggesting that biological variability associated with age remains in the data after harmonization. Critically, there was no significant difference in age prediction using the raw or harmonized CNR (ΔRMSE=7.56±5.53; p=0.1551, permutation test; Δr=−0.06±0.06; p=0.7304, permutation test).

C. NM-MRI Harmonization Improves Statistical Power

The effect of NM-MRI harmonization on statistical power was determined. Specifically, whether harmonization facilitates detection of the underlying age effect was probed using a univariate voxelwise analysis following our previous work. The analyses described herein can be implemented using a compute device, examples of which are described above with reference to FIGS. 1-3.

Figure 13B:
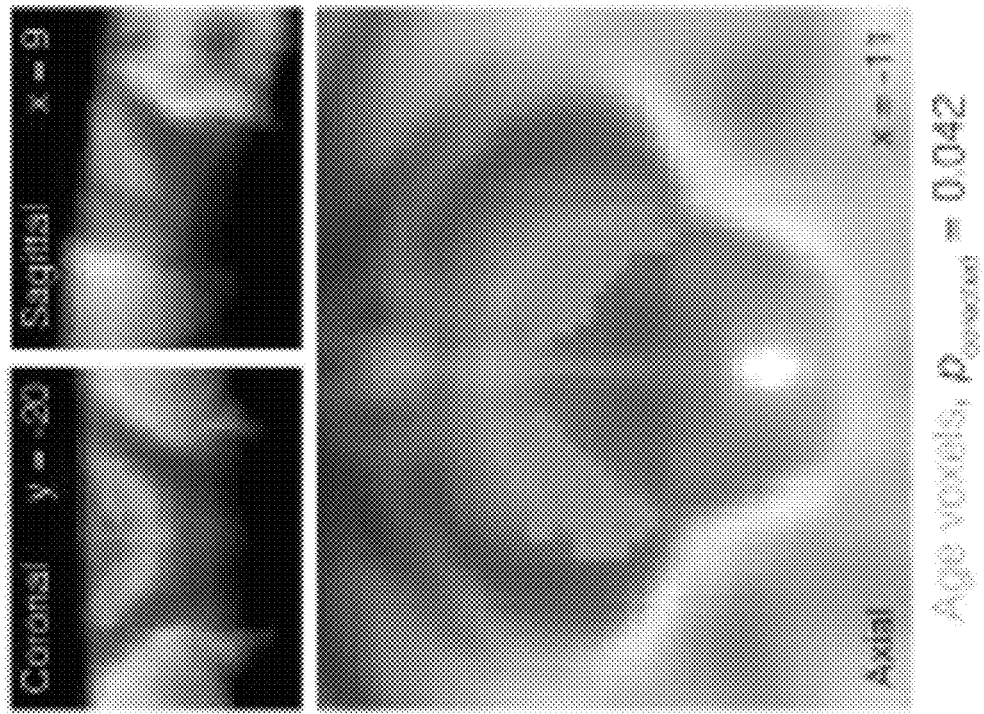
FIGS. 13A and 13B are images representing example imaging data obtained from NM-MRI using multiple imaging sources, before and after harmonization using a data harmonization system, respectively, according to an embodiment.
Figure 13A:
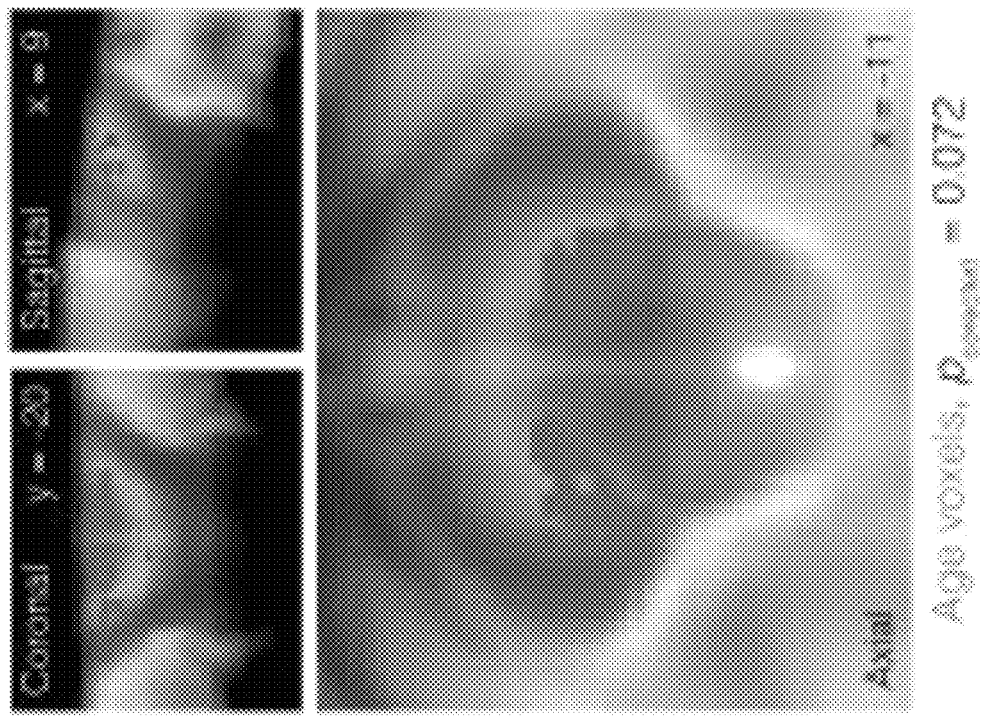
Figure 14:
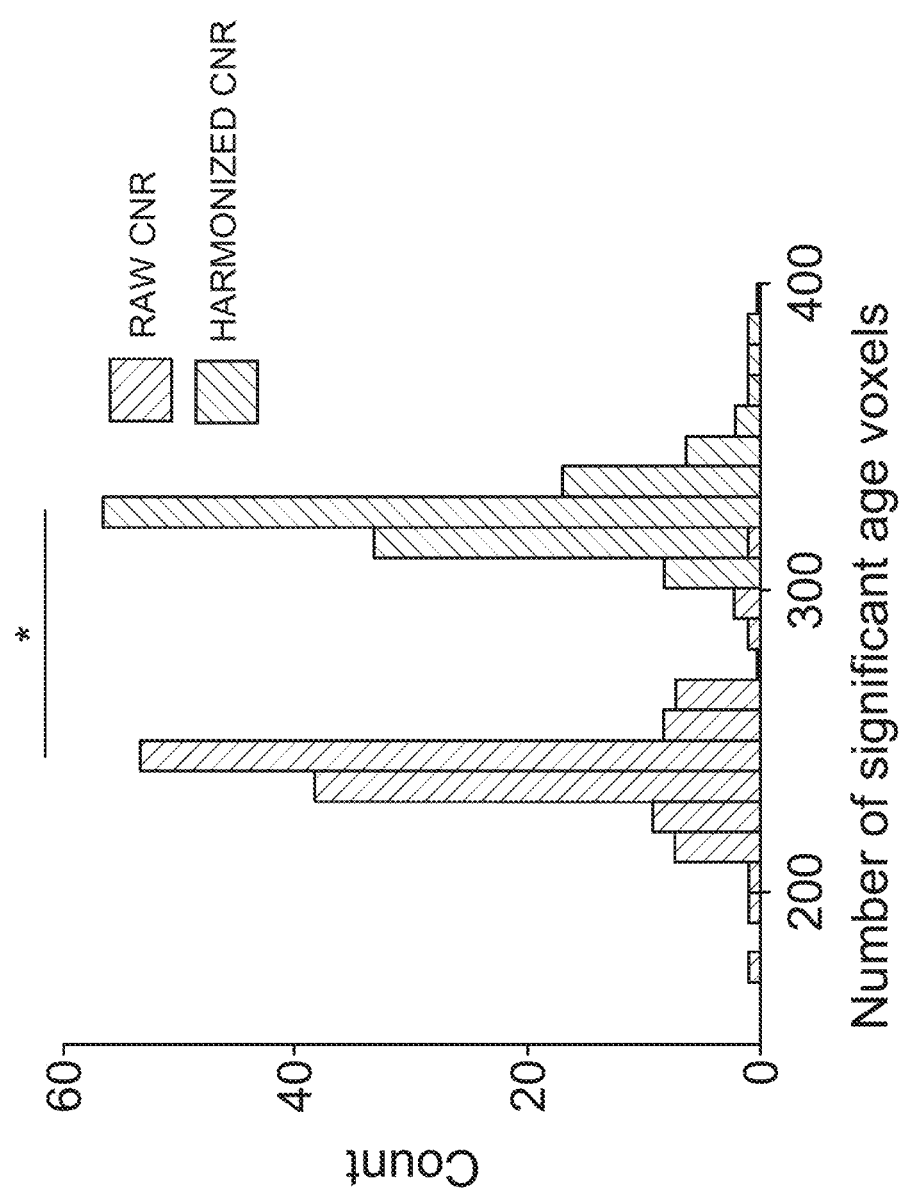
FIG. 14 is a graphical representation of biologically meaningful information in an example imaging data obtained from NM-MRI using multiple imaging sources, before and after harmonization using a data harmonization system, respectively, according to an embodiment.

FIG. 13A shows a map of SN-VTA voxels where the raw NM-MRI CNR positively correlated with age (thresholded at p<0.05, one-sided, voxel level) indicated by the colored magenta pixels overlaid on the average NM-MRI CNR map from all subjects (NM-MRI template). 241 of 1,807 voxels showed an age effect. The central image shows the map of an axial section of the subjects brain while the insets at the top show a coronal section (left) and a sagittal section (right) of the region. FIG. 13B shows a map of SN-VTA voxels where harmonized NM-MRI CNR positively correlated with age (thresholded at p<0.05, one-sided, voxel level) indicated by the colored orange pixels overlaid on the NM-MRI template. 324 of 1,807 voxels showed an age effect. The central image in FIG. 13B also shows the map of an axial section of the subjects brain while the insets at the top show a coronal section (left) and a sagittal section (right) of the region. In the raw CNR, a trend-level age effect in SN-VTA voxels was observed (241 of 1,807 voxels at p<0.05, robust linear regression controlling for gender and MRI scanners, $p_{corrected}$=0.072, permutation test; FIG. 13A). In the harmonized CNR, the extent of the age effect was significantly above chance level (324 of 1,807 voxels at p<0.05, robust linear regression controlling for gender, pcorrected=0.042, permutation test; FIG. 13B). A leave-one-out analysis (i.e., 128 folds) was performed to determine the unbiased correlation between age and the average CNR in age voxels (those voxels showing an age effect), where the age voxels used to read out the average CNR in a given subject were determined in a sample excluding that subject. The unbiased correlation for the raw CNR was small but significant (r=0.19, p=0.031, partial Pearson correlation controlling for gender and MRI scanners), and this effect was numerically (but not statistically; z=0.50, p=0.62, z-test) stronger in the harmonized CNR (r=0.25, p=0.005, partial Pearson correlation controlling for gender). To further investigate the effect of harmonization on statistical power, we compared the number of age-effect voxels for each fold of the leave-one-out analysis between the raw and harmonized CNR. FIG. 14 shows histograms with the number of age-effect voxels over each of the 128 leave-one-out folds for the raw and harmonized CNR. The asterisk (*) denotes p<0.05 for the permutation test comparing the mean number of age voxels from the raw and harmonized CNR. There were consistently less age-effect voxels in the raw CNR (mean±standard deviation: 239.9±16.4 voxels) compared to the harmonized CNR (323.9±12.5 voxels), a difference that reached statistical significance (difference=84.0±9.4 voxels, p=0.002, permutation test; FIG. 14). These results suggested that the effective statistical power is increased in the harmonized CNR using standard analysis procedures, they can be partially due to the decrease in degrees of freedom in the regressions for the raw and harmonized CNR, the latter of which does not include site covariates.

D. NM-MRI Harmonization Improves Reproducibility

The reproducibility of age effects—that is, the ability to observe similar results in different sets of subjects—using subsamples of subjects from our combined dataset was investigated. The analyses described herein can be implemented using a compute device, examples of which are described above with reference to FIGS. 1-3.

Figure 15B:
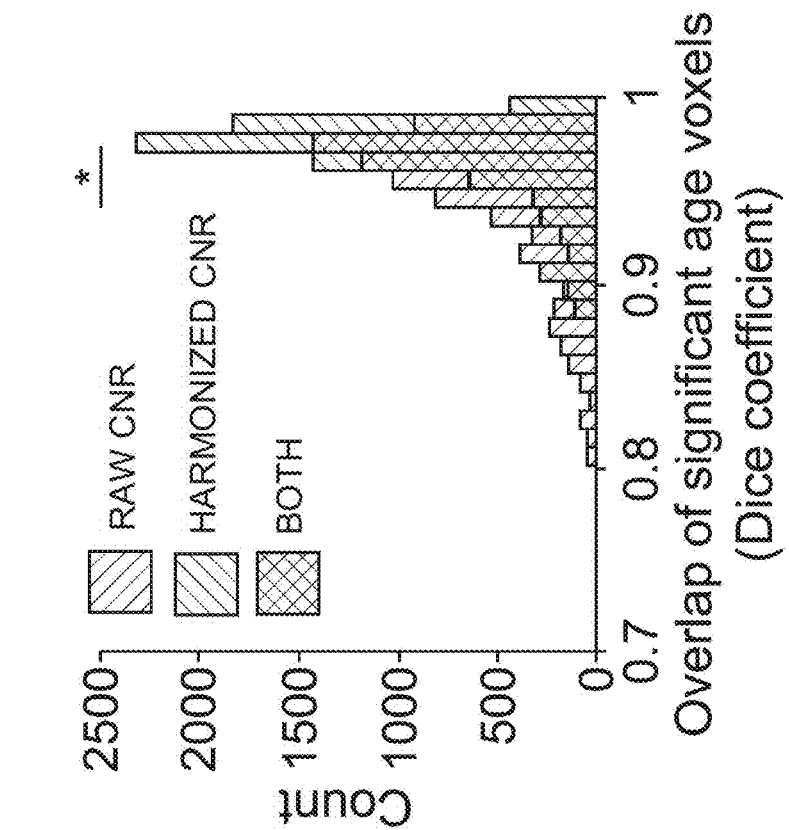
FIG. 15B is a graphical representation of overlap of information associated with biological data in an example imaging data obtained from NM-MRI using multiple imaging sources, before and after harmonization using a data harmonization system, respectively, according to an embodiment.
Figure 15A:
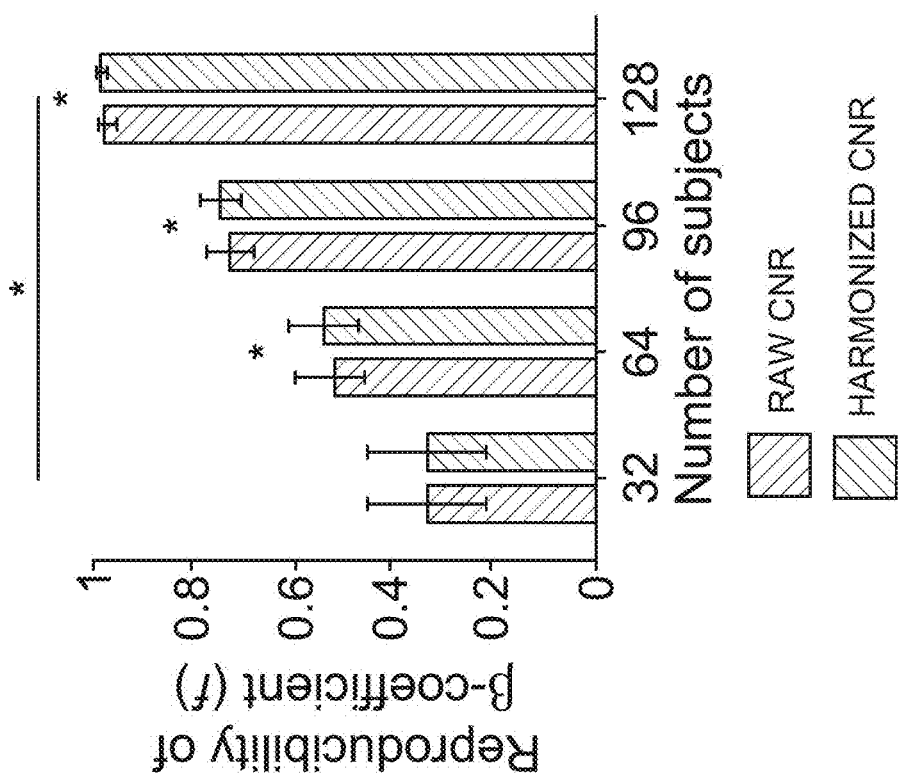
FIG. 15A is a graphical representation of reproducibility of information associated with biological data in an example imaging data obtained from NM-MRI using multiple imaging sources, before and after harmonization using a data harmonization system, respectively, according to an embodiment.

In an SVR, the effect a variable (e.g., age) has on the prediction is coded in the β-coefficients of each voxel and the effect of interest is the multivoxel (spatial) pattern of β-coefficients. To investigate the reliability of the pattern of β-coefficients for predicting age, the 128 subjects were randomly subsampled, and the similarity of the pattern was determined by calculating the spatial correlation between SVR β-coefficients from a given subset of subjects and every other random subset with the same sample size. A significant interaction was found between sample size (n=32, 64, 96, or 128) and CNR type (raw or harmonized) suggesting a significant improvement in reproducibility for the harmonized CNR ($F_{3,7991992}$=9,288.75, $p\ll0.05$, two-way ANOVA; FIG. 15A). FIG. 15A shows bar graphs showing the mean (±SD) reproducibility of β-coefficients of 10-fold cross-validated linear SVR predicting age from 1,000 random 10-fold splits of the data (n=128) or 1,000 random subsets of subjects (n=32, 64, and 96; left). Asterisks (*) denote p<0.05 for a two-way ANOVA comparing the mean correlation of β-coefficients between the raw and harmonized CNR for different sample sizes or permutation tests for pairwise comparisons between the raw and harmonized CNR. FIG. 15B shows histograms indicating the overlap of age-effect voxels over each of the 128 LOO folds for the raw and harmonized CNR (right). The asterisk (*) denotes p<0.05 for the permutation test comparing the median Dice coefficient of the raw and harmonized CNR. Bonferroni post-hoc tests revealed significant increases in reproducibility for the harmonized CNR for all sample sizes except for the smallest subsample: sample sizes of 32 (raw CNR mean±standard deviation: r=0.34±0.11, harmonized CNR: r=0.34±0.12; p=0.817, permutation test; FIG. 15A, 15B), 64 (raw CNR: r=0.53±0.08, harmonized CNR: r=0.55±0.07; p=0.042, permutation test; FIG. 15A, 15B), 96 (raw CNR: r=0.73±0.05, harmonized CNR: r=0.75±0.04; p=0.006, permutation test; FIG. 15A, 15B), and 128 (raw CNR: r=0.99±0.01, harmonized CNR: r=0.99±0.00; p=0.002, permutation test; FIG. 15A, 15B).

As a second test the effect of harmonization on reproducibility, the reproducibility of the age voxels was determined from the univariate voxelwise analysis. We calculated the overlap—measured using the Dice similarity coefficient (Dice, 1945)—in the spatial location of the age voxels for each fold of the leave-one-out analysis. We found lower overlap of age voxels for the raw CNR (median±interquartile range: 0.956±0.046) compared to the harmonized CNR (0.973±0.022), with this difference being statistically significant (difference=−0.016±0.035, p=0.0002, permutation test; FIG. 15A, 15B) and further demonstrating enhanced reproducibility after harmonization.

E. Harmonization via ComBat Coefficients Using Example Systems

Embodiments of the system (e.g., NM-101 or other harmonization algorithms as implemented using compute devices as described above with reference to FIGS. 1-3) can come deployed out of the box with default Combat coefficients for the GE, Siemens, and Philips brand scanners with support for calculating new coefficients for each scanner regardless of the manufacturing brand. Following are some examples use cases.

Onboarding a new facility/scanner: The NM-101 algorithm can come deployed with default combat coefficients calculated for the GE, Siemens, and Philips scanner. The MRIs images scanned from the GE scanner (51 images), Siemens scanner (24 images), and Philips scanner (24 images) were run through the NM-101 algorithm to calculate a voxel map of the SN for each image. These voxel maps, along with the corresponding age and gender for each image are used to calculate the default combat coefficients for the GE, Siemens, and Philips scanners.

When a new organization signs up for the NM-101 algorithm, an administrator can onboard the organization into the system through the NM-101 portal. Using their administrative privileges, they can add a new organization to the system and specify new scanners and their manufacturer model, which will then be linked to a default combat coefficient in the database.

| Scanner Brand | Default Combat Coefficient Link |
|---|---|
| GE | GE default combat coefficient |
| Siemens | Siemens default combat coefficient |
| Philips | Philips default combat coefficient |
| Other | None |

Generate Combat Coefficients: From the administrative page of the NM-101 portal, an administrator can initiate the generation of new combat coefficients for any scanner registered in the system. The calculation of coefficients can be run separately for each scanner and can take up to a minute to complete and update the database. Initiating the process on the NM-101 portal can trigger a REST API exposed by the NM-101 system to initiate the Combat algorithm, which performs the following:

1. Initiate a batch container with the 51 reference voxel maps used to generate the default combat coefficients.
2. Initiate a parameters container with the 51 reference age and genders used to generate the default combat coefficients. Note the reference age and genders align with the reference voxel maps.
3. Query the NM-101 database for all cases that match the criteria {"scanner"=% TARGET_SCANNER %, "organization"=% TARGET ORGANIZATION %}. For each case, multiple SN voxel maps are computed and stored for simultaneous runs.
4. For each case . . .
5. Ignoring any voxel maps that have a NAN value in any of the voxels, compute an average SN voxel map and append it to the batch container.
6. Append the age and gender to the parameters container.
7. Run the combat algorithm to generate new coefficients for the new scanner. Credit to https://github.com/Jfortin1/ComBatHarmonization for NeuroCombat algorithm in Python and Matlab.
8. Save coefficients to NM-101 database and link coefficients to target scanner.

Applying Coefficient: While processing a case through the NM-101 algorithm, before processing the SN voxelwise analysis, the combat coefficients can be applied to SN voxel map the based on the scanner that was used to capture the images. Using the InstitutionName DICOM tag (0008,1010) and StationName DICOM tag (0008,0080) in the MRI images for that case, the system can query the combat coefficient to be used for that case from the NM-101 database. These coefficients can be applied to the SN voxel map to adjust for batch effects from that scanner.

Analysis of data before and after harmonization can be performed to evaluate the effect of data harmonization. Case data from the GE (51 cases), Philips (24 cases), and Siemens (24 cases) scanners were stored in the NM-101 database. The Combat algorithm was initiated to generate coefficients for the GE, Philips, and Siemens scanners using this case data and are stored back into the NM-101 database. These coefficients will be treated as default coefficients for any scans captured with their corresponding scanner manufacturer brand (GE, Philips, Siemens).

Figure 16A:
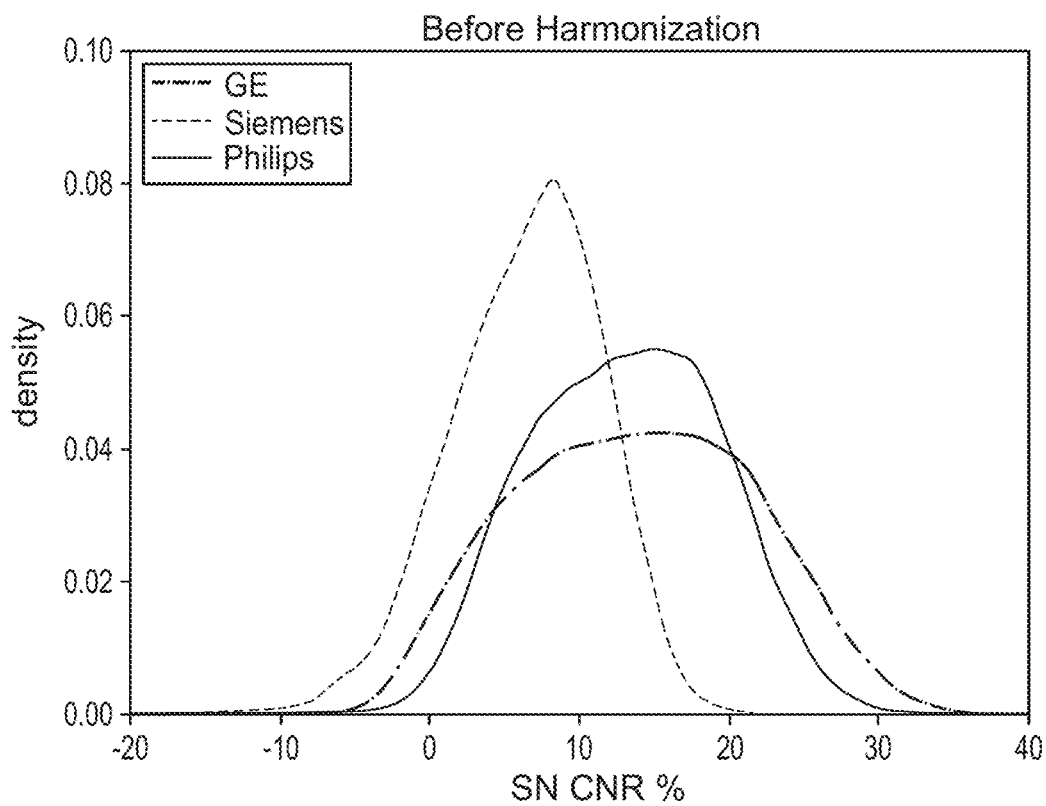
FIGS. 16A and 16B are graphical representations of example imaging data obtained from NM-MRI using multiple imaging sources, before and after harmonization, respectively.
Figure 16B:
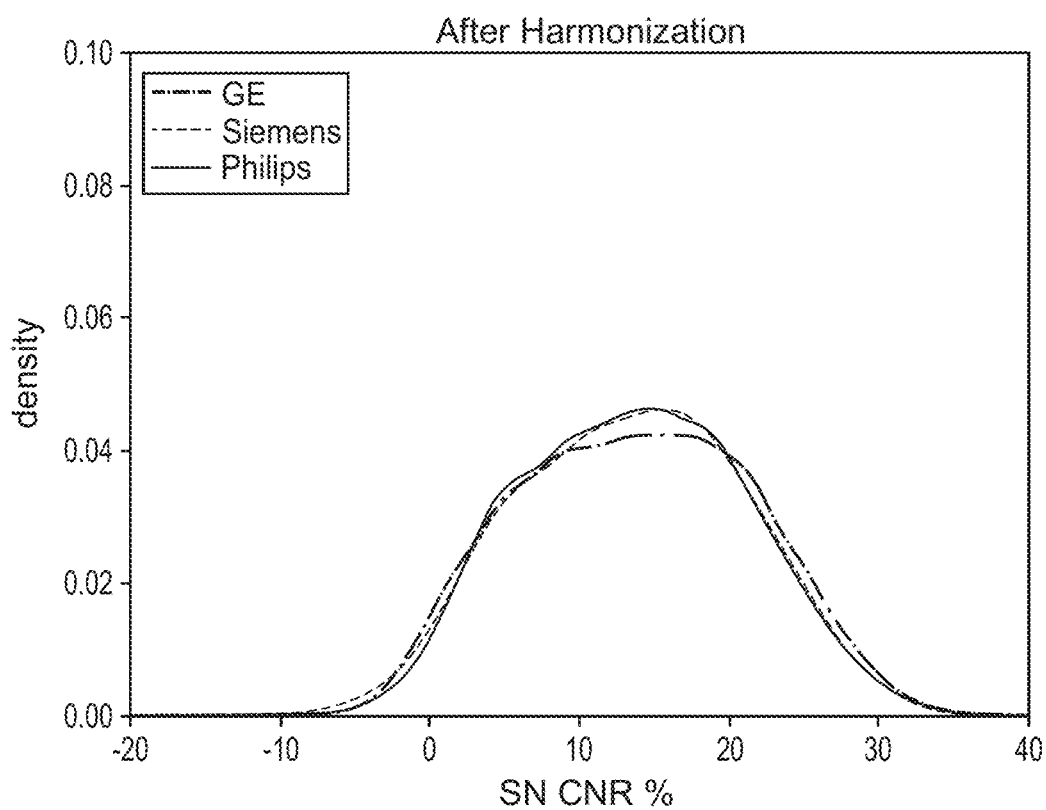
Figure 17A:
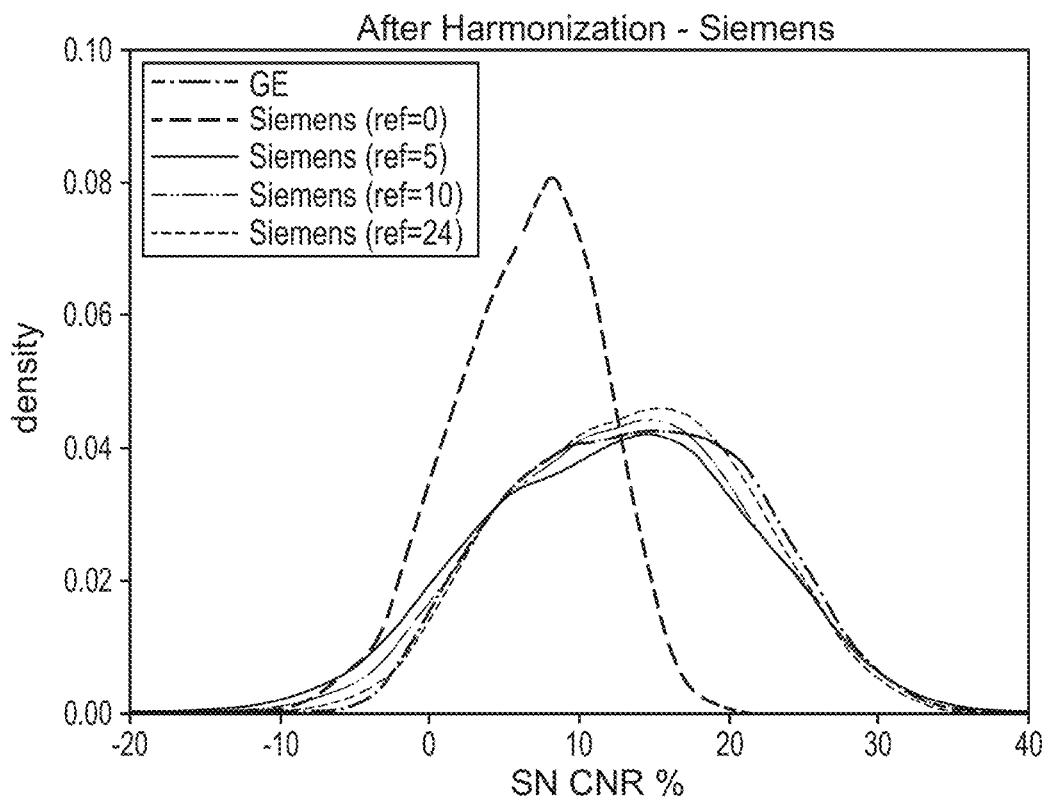
FIGS. 17A and 17B are graphical representations of example imaging data obtained using NM-MRI using imaging sources of two categories, respectively, after harmonization using a data harmonization system, according to an embodiment. The graphs show harmonization based on varying size of data sets.

FIG. 16A shows density plot of the SN CNR% (CNR-NM voxels in the SN) for GE, Siemens, and Philips cases evaluated. FIG. 16B shows new density plots for the same data from same cases as in FIG. 16A, after being harmonized using the combat coefficients retrieved from the NM-101 database for each corresponding scanner (CNR-NM voxels in the SN FIG. 17A).

F. Sample Size Analysis

A study was performed to observe the impact of sample size on the generation of combat coefficients for individual scanners. The analyses described herein can be implemented using a compute device, examples of which are described above with reference to FIGS. 1-3.

Figure 17B:
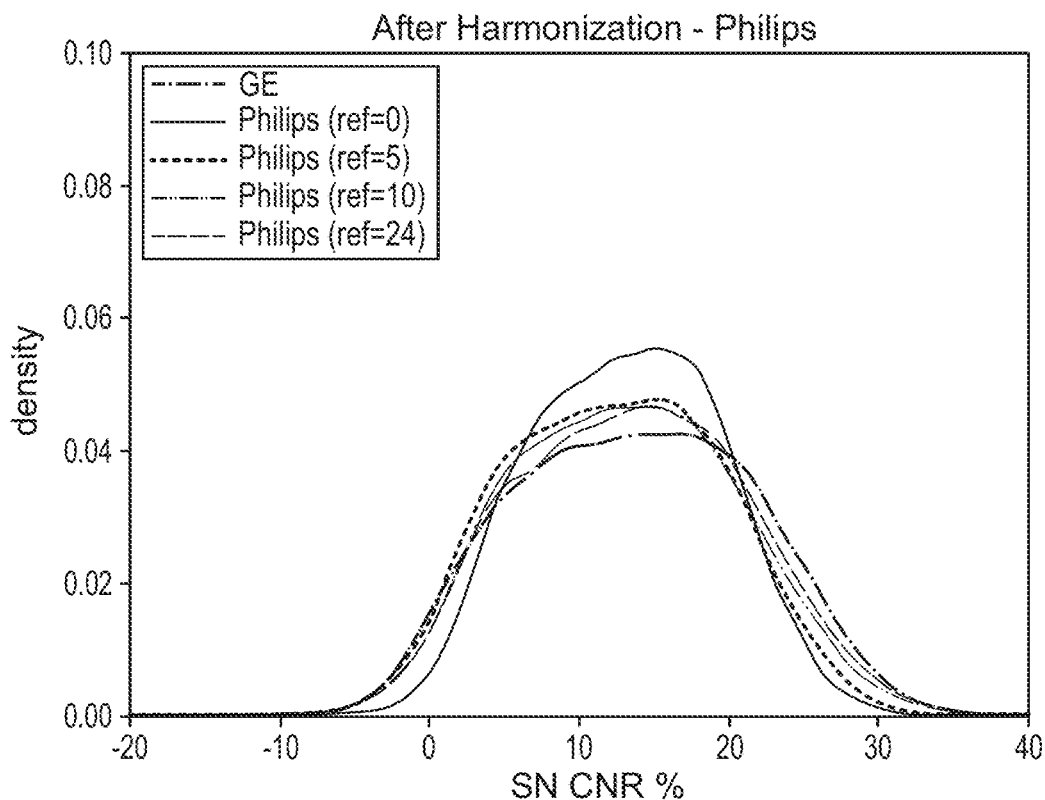

Sets of combat coefficients were generated using a batch of 5 cases, 10 cases, 15 cases, 20 cases, and 24 cases for each scanner type between Siemens and Phillips. Each set of coefficients were then applied to the full set of cases for their corresponding scanner to harmonize the data against the reference GE data set. The resulting SN CNR % density maps are plotted in FIGS. 17A and 17B, respectively.

Figure 18A:
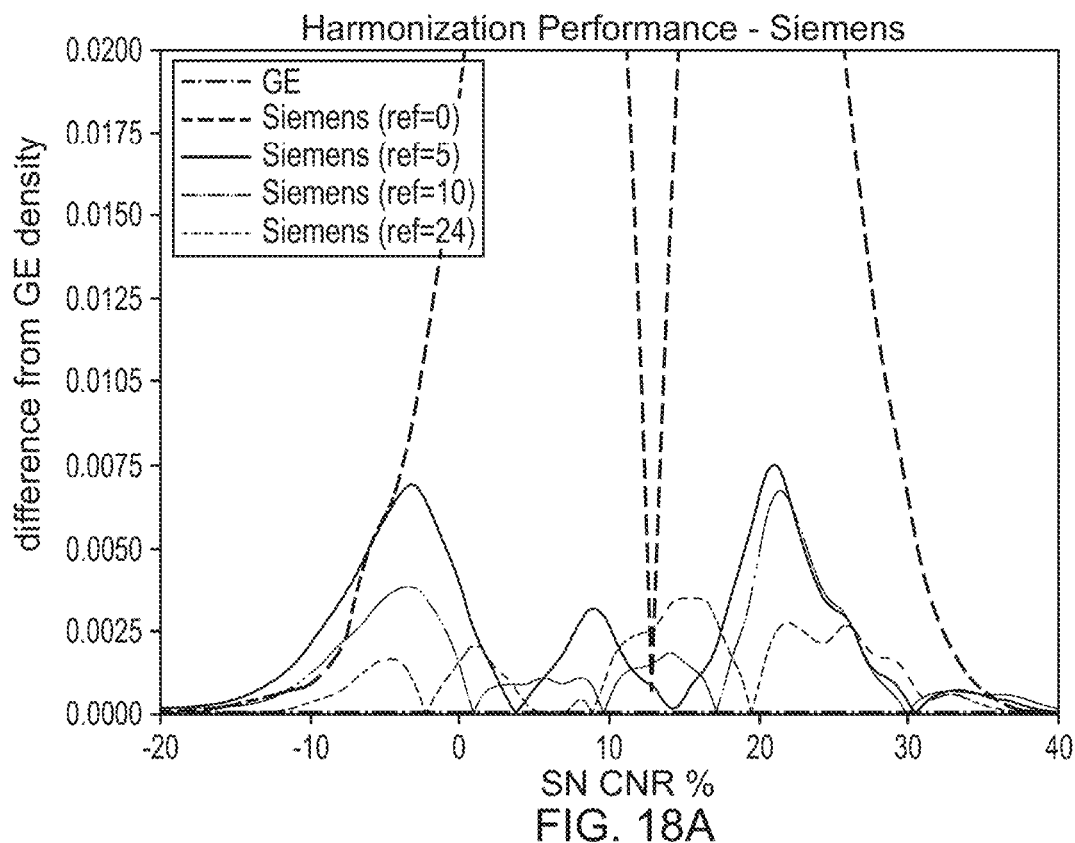
FIGS. 18A and 18B are graphical representations of a measure of harmonization achieved with varying size of data sets obtained using NM-MRI using multiple imaging sources of a first category and a second category, respectively, using a data harmonization system, according to an embodiment.
Figure 18B:
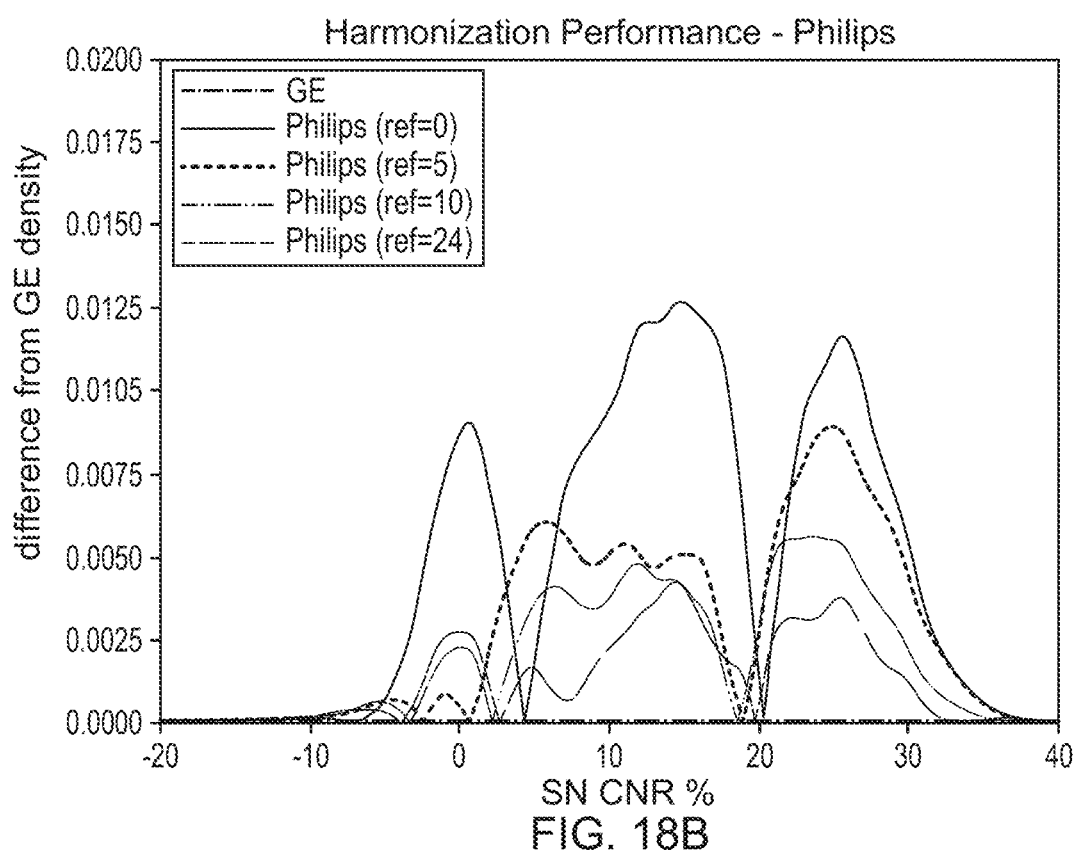

To further demonstrate the improvement of the combat coefficients when using larger batch sets, the resulting SN CNR % data sets are plotted as a difference from the reference GE density value. As the size of the batch set was increased, the difference approached zero, as shown in FIGS. 18A and 18B. For example, the dashed green line in FIG. 18A (ref=0) or the dashed blue line in FIG. 18B (ref=0) is the delta between that data set and GE.

G. Application of Coefficients Generated Using a ComBat Algorithm to Implement a Fully Automated Workflow Suitable for Deployment in a Hospital Setting Challenges applying ComBat to a hospital/clinical setting: Embodiments disclosed above describe a one-time application of a ComBat algorithm to a database as a whole, to prepare the database for analysis with various algorithms, such as the univariate voxelwise analysis and a multivariate voxelwise analysis. The following examples describe an embodiment that includes the adaptation of application of combat algorithm to a hospital/clinic setting. The following examples described herein can be implemented using a compute device, examples of which are described above with reference to FIGS. 1-3.

In the previously discussed applications combat was applied to a clinical trial database once at the end of data collection to create CH-CNR-NM voxels from CNR-NM voxels. This is possible because after the data is collected, there are no immediate modifications, and it is able to be analyzed as a whole at the conclusion (or prespecified midpoint) of a clinical trial. However, in the case of a NM software program deployed across hundreds or thousands of different clinics, there may be a constant influx of NM-MRI data each day. Rather than waiting months to years as is common in large clinical trials, NM data can be reported back to the physician, sometimes on the order of hours post scan. In this case, it may not be feasible to run combat on the entire database every single time that anew patient's NM-MRI was processed by the software Harmonization of NM-MRI data in a hospital setting: NM-MRI data is based on signal intensities which can be highly dependent on the scanner brand and model and parameters under which each scan is collected. This can present a problem for clinicians who may use an automated workflow across multiple machines in hospitals where use of a standard phantom is not feasible. There can be multiple challenges that block the application of NM-MRI to the clinic. Presented here are three examples.

In the first example neuromelanin concentrations and volumes may have to be measured in a patient across two separate timepoints. In this example, a patient receives two NM MRI scans on two different MRI machines with differing parameters, these two scans may have scanner induced variability that confounds the ability to make meaningful comparisons between the two scans for either NM concentrations and volumes or symptom specific voxels or disease specific voxels.

In the second case that a patient receives a NM scan on an MRI machine and that NM scan must be compared to another patient's NM scan that was measured on a different MRI machine, these two scans may have scanner induced variability that confounds the ability to make meaningful comparisons between the two scans for either NM concentrations and volumes or symptom specific voxels or disease specific voxels.

Finally, in a third example, there exists a need to generate and use a standard control CNR-NM dataset. For example a reference dataset for a particular population or age group. To generate such a reference dataset, involves the analysis of a database to generate a standard control level of neuromelanin concentrations and volumes or standard voxelwise patterns. However, the database may include CNR-NM MRI data that was acquired on different MRI machines with non-optimized parameters.

Applying ComBat generated Coefficients: Embodiments disclosed include two solutions to harmonize patient NM MRI data using combat generated coefficients in a manner suitable for deployment in a fully automated clinical environment. These combat generated coefficients can be utilized on all future NM MRI data so that there is no need to run combat on further NM MRI data.

In an example implementation of the first solution, each MRI scanner is assigned a specific adjustment factor that brings it into alignment with a standard reference MRI scanner. This adjustment factor is generated by acquiring a number of MRI scans on that scanner. These scans are then stored in a database and the combat algorithm is run on the processed CNR-NM data stored in that database and the CNR-NM data from the reference scanner database. This results in an MRI scanner specific adjustment factor (termed a scanner specific factor) that is unique to each individual MRI scanner. The scanner specific factor is then stored in a database of scanner factors. This process of generating a scanner specific factor for onboarding a new MRI scanner to use the fully automated software is termed scanner specific harmonization and detailed in FIGS. 6-8.

Following the completion of the scanner specific harmonization period, each time a new MRI is acquired on that scanner, the scanner specific factor is applied to the new CNR-NM data to harmonize it before it can be reported to the physician or used to run statistical tests such as the voxelwise analysis method (FIG. 8). In this case, combat is not run on any new MRI scans following the scanner specific harmonization period.

In an example implementations of the second solution, NM-MRI data can be acquired on a machine for which no scanner specific coefficient exists, and it may not be possible to run a number of test cases to harmonize the scanner and generate a new scanner specific coefficient. Under such circumstances, the software can use a separate coefficient termed a vendor specific coefficient.

Vendor specific coefficients can be generated by acquiring a number of scans on MRI machines from each vendor. In this case, the scans may be acquired on different MRI machine models within a specific vendor group (for example, different MRI models manufactured by Philips). Combat can then run on the database of CNR-NM voxels acquired from MRI machines from only one specific vendor and the resulting data can be compared to CNR-NM voxels from a reference MRI vendor database (in this case the GE database). The resulting output from the comparison can be used to generate a vendor specific adjustment factor termed a vendor specific coefficient.

In the absence of a scanner specific coefficient a vendor specific coefficient can then be applied to any new scans from an MRI machine of the same vendor that has not yet undergone scanner specific harmonization. In this case, combat is not applied to any of the scans from the new scanner and the coefficient takes the place of implementing combat. This allows harmonization of CNR-NM voxels to generate CH-CNR-NM voxels solely based on using the coefficient and without having to run combat directly on those specific voxels. One advantage of the vendor specific adjustment factor is that the CNR-NM voxels can be harmonized to CH-CNR-NM even in the absence of a scanner specific adjustment factor. In an example implementation, to determine an optimal number of MRI scans that can be used to generate an accurate scanner specific or vendor specific adjustment factor, combat coefficients were generated from 5, 10, and 24 CNR-NM scans. This is detailed in FIGS. 16-18 and the description associated with FIGS. 16-18.

Advantages: Since the combat coefficients result in CH-CNR-NM voxels, the following advantages also apply.

Voxelwise analysis of a database of CH-CNR-NM voxels that includes voxels measured from different MRI machines or the same MRI machine with different parameters can result in improved power to detect voxel based patterns than would otherwise be achieved using the voxelwise analysis on CNR voxels in the same database that have not undergone harmonization. In one example, application of the voxelwise analysis method to a database of CH-CNR voxels results in a higher statistical power to detect voxels that are significantly associated with either a specific diagnosis (disease specific voxels), or a specific symptom (symptom specific voxels) than application of the voxelwise analysis to CHR voxels alone.

Voxelwise analysis of a database of CH-CNR-NM voxels that includes voxels measured from different MRI machines or the same MRI machine with different parameters can result in improved power to detect differences in neuromelanin concentrations and volumes than would otherwise be achieved using the voxelwise analysis on CNR voxels in the same database that have not undergone harmonization.

Voxelwise analysis of a database of CH-CNR-NM voxels that includes voxels measured from different MRI machines or the same MRI machine with different parameters can result in improved reproducibility to detect voxel based patterns than would otherwise be achieved using the voxelwise analysis on CNR-NM voxels in the same database that have not undergone harmonization. In one example, application of the voxelwise analysis method to a database of CH-CNR-NM voxels results in a higher statistical power to detect voxels that are significantly associated with either a specific diagnosis (disease specific voxels), or a specific symptom (symptom specific voxels) than application of the voxelwise analysis to CHR-NM voxels alone.

Voxelwise analysis of a database of CH-CNR-NM voxels that includes voxels measured from different MRI machines or the same MRI machine with different parameters can result in improved reproducibility to detect differences in neuromelanin concentrations and volumes than would otherwise be achieved using the voxelwise analysis on CNR voxels in the same database that have not undergone harmonization.

Multivariate Voxelwise analysis of a database of CH-CNR-NM voxels that includes voxels measured on different MRI machines or the same MRI machine with different parameters can result in improved ability to perform multivariate predictions than would otherwise be achieved using the voxelwise analysis on CNR voxels in the same database that have not undergone harmonization. In this example, age . . . (figure X).

In all of the above listed implementations, the voxelwise analysis can be univariate or multivariate Embodiments disclosed include method for harmonizing NM-MRI data across sites and scanners to remove nonbiological variability due to factors such as hardware and software differences. In addition to effectively removing nonbiological variability, the harmonization method maintains biologically relevant variability (e.g., age effects) while increasing both reproducibility and statistical power. The disclosed systems and methods represent a first approach for harmonizing NM-MRI data, an important step to enable and enhance large-scale multisite studies.

Implementing the ComBat algorithm successfully reduced systematic biases associated with scanner across multiple sites in which acquisition protocols were not fully harmonized. Significant differences were observed in SN-VTA CNR values between two GE scanners (MR750 and Signa Premier) both at the same institute (Columbia University) but the MR750 data were acquired with a slice thickness of 3 mm while the Signa Premier data were acquired with a slice thickness of 1.5 mm. The ability of ComBat to harmonize these data suggested that the 'batch' effects can envelop all nonbiological sources of variability and can alleviate the need to have perfectly matched acquisition protocols which may not be possible due to software and hardware limitations.

In addition to removing nonbiological variance from the NM-MRI data, maintaining biologically meaningful variability can also be of importance. A successful method of harmonization to facilitate multisite studies focused on biomarker development can involve maintaining the relevant biological variability. In the case of an NM-MRI biomarker for diagnosis of Parkinson's disease, schizophrenia, or any other neuropsychiatric condition, this can typically be the effect of diagnosis. Other biomarkers may instead focus on prediction of treatment response or other clinically relevant outcomes. Embodiments and examples disclosed show a proof-of-concept demonstration that ComBat can maintain biologically meaningful variability by showing that it preserves variability associated with age among healthy individuals. The disclosed study represent, to the inventors' knowledge, the first application of MVPA to NM-MRI data. SVM methods were used to successfully classify MRI scanner from SN-VTA CNR in the raw CNR and SVR to successfully predict age from SN-VTA CNR in both the raw and harmonized CNR.

In conclusion, disclosed herein are systems, devices, and methods for using ComBat to harmonize NM-MRI data that effectively reduces nonbiological variability while maintaining biologically relevant variability and producing improvements in reproducibility and statistical power. ComBat harmonization is likely to benefit studies even if acquisition parameters across different scanners are harmonized prior to data collection—as recommended for multisite studies. But, importantly, the current data suggest that harmonization is unlikely to be harmful or obscure the biological effects under investigation, at least as long as they are identified a priori. This approach can pave the way for large-scale multisite studies to develop NM-MRI-based biomarkers.

Although various embodiments have been described as having particular features and/or combinations of components, other embodiments are possible having a combination of any features and/or components from any of embodiments as discussed above.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In this disclosure, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The use of any and all examples, or exemplary language ("e.g.," "such as," "including," or the like) provided herein, is intended merely to better illuminate the embodiments and does not pose a limitation on the scope of the embodiments or the claims.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Also, various concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A method of harmonizing a neuromelanin dataset using a vendor specific combat coefficient, comprising:
   measuring a first level of neuromelanin associated with a first dataset obtained using a set of MRI machines manufactured by a first vendor;
   measuring a second level of neuromelanin associated with second dataset obtained using a reference MRI machine manufactured by a second vendor different from the first vendor;
   implementing a machine learning (ComBat) algorithm to generate a vendor specific coefficient associated with the set of MRI machines, the vendor specific coefficient being based on at least one of (1) the first level of neuromelanin associated with a set of MRI machines or (2) the second level of neuromelanin associated with reference MRI machine;
   obtaining a third dataset associated with a first MRI machine manufactured by the first vendor; and
   applying the vendor specific coefficient directly on the third dataset from the first MRI machine manufactured by the first vendor to measure an adjusted third level of neuromelanin associated with first MRI machine compared to at least one of (1) the second level of neuromelanin associated with the reference MRI machine or (2) the second dataset.

2. A method of assessing the neuromelanin concentration in a region of interest of the brain of a subject, comprising:
   performing a Neuromelanin-Magnetic Resonance Imaging (NM-MRI) scan on a subject;
   acquiring a neuromelanin dataset from the NM-MRI scan;
   optionally encrypting the neuromelanin dataset;
   uploading the neuromelanin dataset to a remote server;
   optionally decrypting the dataset;
   harmonizing the dataset by (i) running a combat algorithm on the entire dataset to generate and apply a coefficient, or (ii) applying a scanner specific coefficient to the dataset, or (iii) applying a vendor specific coefficient to the dataset;
   performing an analysis of the neuromelanin dataset, wherein the analysis comprises one or more of:
   (i) comparing the neuromelanin dataset with one or more previously acquired neuromelanin datasets from the said subject;
   (ii) comparing the neuromelanin dataset with a control dataset;
   (iii) comparing the neuromelanin dataset with one or more previously acquired neuromelanin datasets from different subjects;
   generating a report comprising the neuromelanin analysis; and
   uploading the report to remote server.

3. The method of claim 2, wherein the NM dataset prior to adjustment with combat includes Contrast Ratio-Neuromelanin (CNR-NM) voxels.

4. The method of claim 2, wherein the NM dataset after adjustment with combat comprises ComBat Harmonized Contrast Ratio-Neuromelanin (CH-CNR-NM) voxels.

5. The method of claim 2, wherein the NM dataset includes measures indicating presence of Neuromelanin in a midbrain region including dopaminergic pathways of a subject.

6. The method of claim 2, where the voxel-wise analysis procedure is performed on CH-CNR-NM voxels.

7. An apparatus, comprising:
a memory; and
a processor operatively coupled to the memory, the processor configured to:
receive information associated with an imaging source;
receive a first dataset including a first plurality of images associated with the imaging source, each image in the plurality of images includes a set of voxels;
apply a mask on the first plurality of images to generate a voxel map, the voxel map being based in an average of values associated with a subset of voxels from the set of voxels;
calculate a first set of measures based on the voxel map, the first set of measures being based on indications of a presence of a biomarker in the plurality of images based on which the voxel map was generated;
provide the first set of measures to a data harmonization algorithm, the data harmonization algorithm configured to calculate a set of coefficients, the set of coefficients when applied to the first set of measures configured to transform the first set of measures into a harmonized second set of measures, the second set of measures having a reduced variability associated with one or more identified sources of variability, compared to the first set of measures;
receive the second set of measures and the set of coefficients associated with the transformation of the first set of measures into the second set of measures; and
link and store the second set of measures and the set of coefficients with the information associated with the imaging source.

8. The apparatus of claim 7, wherein the processor is configured to calculate the first set of measures by determining contrast to noise ratio (CNR) associated with each voxel from the subset of voxels, the CNR associated with each voxel being based on a difference between a first signal intensity associated with that voxel and a second signal intensity associated with a reference voxel, the reference voxel known to include minimal content of the biomarker.

9. The apparatus of claim 7, wherein the biomarker is Neuromelanin.

10. The apparatus of claim 7, wherein the imaging source includes at least one of an MRI scanner type, an MRI scanner, or a subject of an MRI scan.

11. The apparatus of claim 7, wherein the set of coefficients is such that second set of measures has a reduced variability associated with one or more identified sources of variability, including identified sources of additive and multiplicative variability.

12. A non-transitory processor-readable medium storing code representing instructions to be executed by a processor, the instructions comprising code to cause the processor to:
receive a dataset including a plurality of images;
receive information associated with an imaging source associated with the dataset;
compute a first set of measures based on the plurality of images;
search a database to determine a set of coefficients associated with the imaging source, the set of coefficients configured to transform the first set of measures into a harmonized second set of measures, the second set of measures having a reduced variability associated with one or more identified sources of variability, compared to the first set of measures;
obtain the set of coefficients associated with the imaging source;
apply the set of coefficients to the first set of measures to generate the second set of measures having the reduced variability associated with the one or more identified sources of variability; and
store the second set of measures in association with the set of coefficients and the information associated with an imaging source.

13. The non-transitory processor-readable medium of claim 12, wherein the imaging source includes at least one of a brand of scanning equipment used to acquire the plurality of images, an identity of scanning equipment used to acquire the plurality of images, or a subject being scanned to acquire the plurality of images.

14. The non-transitory processor-readable medium of claim 12, wherein the instructions include code to cause the processor to:
determine, in response to the search, an absence of the set of coefficients associated with the imaging source;
provide the first set of measures to a data harmonization algorithm, the data harmonization algorithm configured to generate the set of coefficients to transform the first set of measures into a harmonized second set of measures.

15. The non-transitory processor-readable medium of claim 12, wherein the instructions include code to cause the processor to:
apply a mask to the plurality of images, the mask being based on a region of interest; and
compute, based on the application of the mask, an average voxelmap associated with the region of interest, the first set of measures being computed based on the average voxelmap.

16. The non-transitory processor-readable medium of claim 15, wherein the region of interest is the Substantia Nigra (SN) region.

17. The non-transitory processor-readable medium of claim 12, wherein the plurality of images is acquired using a biomarker specific MRI.

18. The non-transitory processor-readable medium of claim 17, wherein the biomarker is Neuromelanin (NM).

* * * * *